US006869671B1

(12) United States Patent  (10) Patent No.: US 6,869,671 B1
Crouse et al.  (45) Date of Patent: Mar. 22, 2005

(54) ENABLING NANOSTRUCTURED MATERIALS VIA MULTILAYER THIN FILM PRECURSOR AND APPLICATIONS TO BIOSENSORS

(75) Inventors: Michael M. Crouse, Walkerton, IN (US); Albert E. Miller, Notre Dame, IN (US); Juan Jiang, Mishawaka, IN (US); David T. Crouse, Notre Dame, IN (US); Subash C. Basu, Granger, IN (US)

(73) Assignee: University of Notre Dame, Notre Dame, IN (US)

( * ) Notice: Subject to any disclaimer, the term of this patent is extended or adjusted under 35 U.S.C. 154(b) by 0 days.

(21) Appl. No.: 10/449,618

(22) Filed: Jun. 2, 2003

Related U.S. Application Data

(60) Provisional application No. 60/384,386, filed on Jun. 3, 2002.

(51) Int. Cl.⁷ ................................................. B32B 3/00
(52) U.S. Cl. ..................... 428/304.4; 428/209; 428/457; 428/620; 428/632; 428/639; 428/640; 428/641; 428/650; 428/651; 428/652; 428/654; 428/660; 428/668; 428/670; 428/672; 428/307.3; 428/312.2; 428/312.8; 428/314.8; 428/315.5; 428/315.7; 428/315.9; 428/317.1; 428/317.7; 428/318.4; 428/319.1; 428/432; 428/446; 428/469; 428/472; 428/472.2; 428/689; 428/699; 428/701; 428/702; 977/DIG. 1
(58) Field of Search .............................. 428/304.4, 209, 428/457, 620, 632, 639–641, 650–652, 654, 660, 668, 670, 672, 307.3, 312.2, 312.8, 314.8, 315.5, 315.7, 315.9, 317.1, 317.7, 318.4, 319.1, 432, 446, 469, 472, 472.2, 689, 699, 701, 702; 977/DIG. 1

(56) References Cited

PUBLICATIONS

Memming, "Charge Transfer Processes at the Semiconductor–Liquid Interface," *Semiconductor Electrochemistry*, 2001, Chapter 7, pp. 151–209.
Bard et al., "Potential Sweep Methods," *Electrochemical Methods*, 2000, Chapter, 6, pp. 239–256.
Vetter, "The Theory of Overvoltage," *Electrochemical Kinetics*, 1967, Chapter 2, pp. 104–107, and "Mixed Potentials and Electrolytic Corrosion," Chapter 5, pp. 157–166.
Masuda et al., "Self–Ordering of Cell Arrangement of Anodic Porous Alumina Formed in Sulfuric Acid Solution," *J. Electrochem. Soc.*, May 1997, vol. 144, No. 5, pp. 127–130.
Park et al., "Microstructures and interdiffusions of Pt/Ti electrodes with respect to annealing in the oxygen ambient," *J. Mater. Res.*, Jul. 1995, vol. 10, No. 7, pp. 1790–1794.

Xu et al., "Preparation of II–IV group semiconductor nanowire arrays by dc electrochemical deposition in porous aluminum oxide templates," *Pure Applied Chemistry*, 2000, vol. 72, Nos. 1–2, pp. 127–135.
Kweon et al., "Platinum Hillocks in Pt/Ti Film Stacks Deposited on Thermally Oxidized Si Substrate," *Jpn. Journal of Applied Physics*, Oct. 2001, vol. 40, pp. 5850–5855.
O'Sullivan et al., "The morphonolgy and mechanism of formation of porous anodic films on aluminum," *Proc. Roy. Soc. Lond. A.*, 1970, pp. 511–543.
Colgan, "A review of thin–film aluminide formation," *Materials Science Reports*, 1990, vol. 5, pp. 1–44.
Moussa et al., "Non–parametric regression in curve fitting," *The Statistician*, 1992, vol. 41, Issue 2, pp. 209–225.
Colgan et al., "Void formation in thin Al films," *Applied Physics Letters*, Aug. 1987, vol. 51, pp. 424–426.
Comer, "Electron diffraction data on new compounds in the system platinum–aluminum," *Acta Cryst.*, 1964, vol. 17, pp. 444–445.
Colgan et al., "Interfacial reaction–induced morphological instabilities in thin Al/Pt and Al/Pd films," *J. Mater Res.*, Sep./Oct. 1987, vol. 2, No. 5, pp. 557–567.
Lindquist et al., "Charge Transport in Nanostructured Thin–film Electrodes," *Electrochemistry of Nanomaterials*, Mar. 2001, Chapter 6, pp. 169–200.
Murray, "The Pt–Ti (Platinum–Titanium) System," *Bull. Alloy Phase Diagrams*, 1982, p. 329.
Fujishima et al., "Electrochemical Photolysis of Water at a Semiconductor Electrode," *Nature*, Jul. 1972, vol. 238, pp. 37–38.
Xu et al., "Preparation of CdS Single–Crystal Nanowires by Electrochemically Induced Deposition," *Advanced Materials*, 2000, vol. 12, No. 7, pp. 520–522.
Colgan et al., "Void formation in thin Al films," *Applied Physics Letters*, Aug. 1987, vol. 51, No. 6, pp. 424–426.
Radi et al., "Diffusion coefficient of Al in metastable, amorphous Al–Pt phase," *Applied Physics Letters*, Nov. 1998, vol. 73, No. 22, pp. 3220–3222.

(List continued on next page.)

*Primary Examiner*—Deborah Jones
*Assistant Examiner*—Ling Xu
(74) *Attorney, Agent, or Firm*—Jagtiani + Guttag

(57) ABSTRACT

A thin film based nanoporous alumina template has been developed which allows the in situ removal of an electrically insulating alumina barrier layer at the pore bases. This barrier free nanoporous system has great utility for electrodeposition of a wide variety of nanowire materials. An exemplary multilayer thin film precursor is provided comprising Al (anodization layer), Ti (diffusion barrier) and Pt (active electrode) on a Si substrate. Aluminum anodization in sulfuric acid with a subsequent applied voltage ramping program produces a Pt electrode at the base of the nanopores without the additional steps of alumina removal, barrier layer dissolution, and metal deposition onto the pore bottoms.

53 Claims, 32 Drawing Sheets

PUBLICATIONS

Masuda et al., "Highly ordered nanochannel–array architecture in anodic alumina," *Applied Physics Letters,* Nov. 1997, vol. 71, No. 19, pp. 2770–2772.

Crouse et al., "Self–ordered pore structure of anodized aluminum on silicon and pattern transfer," *Applied, Physics Letters,* Jan. 2000, vol. 76, No. 1, pp. 49–51.

Thamida et al., "Nonoscale pore formation dynamics during aluminum anodization," *Chaos,* Mar. 2002, vol. 12, No. 1, pp. 240–251.

Brereton et al., "Nucleation in small capillary tubes," *Chemical Physics,* 1998, vol. 230, pp. 253–265.

Xu et al., "Preparation and characterization of CdS nanowire arrays by dc electrodeposit in porous anodic aluminum oxide templates," *Chemical Physics Letters,* Jul. 2000, vol. 325, pp. 340–344.

Peng et al., "Synthesis of highly ordered CdSe nanowire arrays embedded in anodic alumina membrane by electrodeposition in ammonia alkaline solution," *Chemical Physics Letters,* Aug. 2001, vol. 343, pp. 470–474.

Albella et al., "A Theory of Avalanche Breakdown during Anodic Oxidation," *Electrochimica Acta,* 1987, vol. 32, No. 2, pp. 255–258.

Delplancke et al., "Galvanostatic Anodization of Titanium—1. Structures and Compositions of the Anodic Films," *Electrochimica Acta,* 1988, vol. 33, No. 11, pp. 1539–1549.

Serebrennikova et al., "Characterization of porous aluminum oxide films by metal electrodeposition," *Electrochimica Acta,* 1997, vol. 42, No. 1, pp. 145–151.

Schultze et al., "Stability, reactivity and breakdown of passive films. Problems of recent and future research," *Electrochimica Acta,* 2000, vol. 45, pp. 2499–2513.

Bak et al., "Photo–electrochemical properties of the TiO2–Pt system in aqueous solutions," *International Journal of Hydrogen Energy,* 2002, vol. 27, pp. 19–26.

Bak et al., "Photo–electrochemical hydrogen generation from water using solar energy. Materials–related aspects," *International Journal of Hydrogen Energy,* 2002, vol. 27, pp. 991–1022.

Radi et al., "Kirkendall voids and the formation of amorphous phase in the Al–Pt thin–film system prepared by high–temperature successive deposition," *Journal of Applied Physics,* Apr. 1996, vol. 79, No. 8, pp. 4096–4100.

Murarka et al., "Thin–film interaction in aluminum and platinum," *Journal of Applied Physics,* Dec. 1976, vol. 47, No. 12, pp. 5175–5181.

Hickmott, "Polarization measurements in anodized Al–Al$_2$O$_3$–Au diodes," *Applied Physics Letters,* Nov. 1999, vol. 75, No. 19, pp. 2999–3001.

Hickmott, "Polarization and Fowler—Nordheim tunneling in anodized Al–Al$_2$O$_3$–Au diodes," *Journal of Applied Physics,* Jun. 2000, vol. 87, No. 11, pp. 7903–7912.

Hickmott, Voltage–dependent dielectric breakdown and voltage–controlled negative resistance in anodized Al–Al$_2$O$_3$–Au diodes, *Journal of Applied Physics,* Sep. 2000, vol. 88, No. 5, pp. 2805–2812.

Chen et al., "Silver telluride nanowires prepared by dc electrodeposition in porous anodic alumina templates," *Journal of Materials Chemistry,* 2002, vol. 12, pp. 2435–2438.

Horrocks et al., "Scanning Electrochemical Microscopy. 25. Application to Investigation of the Kinetics of Heterogeneous Electron Transfer at Semiconductor (Wse$_2$ and Si) Electrodes," *Journal of Physical Chemistry,* 1994, vol. 98, pp. 9106–9114.

Xu et al., "Electrochemical Preparation of CdSe Nanowire Arrays," *Journal of Physical Chemistry,* 2000, vol. 104, pp. 5061–5063.

Tremiliosi–Filho et al., "Characterization and Significance of the Sequence of Stages of Oxide Film Formation at Platinum Generated by Strong Anodic Polarization," *Langmuir,* 1992, vol. 8, pp. 658–667.

Sul et al., "The electrochemical oxide growth behaviour on titanium in acid and alkaline electrolytes," *Medical Engineering & Physics,* 2001, vol. 23, pp. 329–346.

Saguès et al., "Growth and forms in quasi–two–dimensional electrocrystallization," *Physics Reports,* 2000, vol. 337, pp. 97–115.

Conway, "Electrochemical Oxide Film Formation at Noble Metals as a Surface–Chemical Process," *Progress in Surface Science,* 1995, vol. 49, No. 4, pp. 331–452.

Martin, "Nanomaterials: A Membrane–Based Synthetic Approach," *Science,* Dec. 1994, vol. 266, Issue 5193, pp. 1961–1966.

Yang et al., "Anodic alumina template on Au/Si substrate and preparation of CdS nanowires," *Solid–State Communications,* 2002, vol. 123, pp. 279–282.

Tatarenko et al., "Geometry and element composition of a nanoscale field emission array formed by self–organization in porous anodic aluminum oxide," *Solid–State Electronics,* 2001, vol. 45, pp. 1009–1016.

Vorobyova et al., "Study of pillar microstructure formation with anodic oxides," *Thin Solid Films,* 1998, vol. 324, pp. 1–10.

Lee et al., "Effects of a titanium interlayer on the formation of platinum silicides," *Thin Solid Films,* 1997, vol. 303, pp. 232–237.

Buchanan et al., "Foodborne Disease Significance of *Escherichia coli* O157:H7 and Other Enterohemorrhagic *E. coli*," *FoodTechnology,* Oct. 1997, vol. 51, No. 10, pp. 69–76.

Ghindilis et al., "Immunosensors: electrochemical sensing and other engineering approaches," *Biosensors & Bioelectronics,* 1998, vol. 13, No. 1, pp. 113–131.

Göpel, "Chemical Sensing, Molecular Electroncis and Nanotechnology: Interface Technologies Down to the Molecular Scale," *Sensors and Actuators,* 1991, vol. 4, pp. 7–21.

Griffin et al., "The Epidemiology of Infections Caused by *Escherichia coli* O175:H7, Other Enterohemorrhagic *E. coli,* and the Associated Hemolytic Uremic Syndrome," *Epidermiologic Reviews,* 1991, vol. 10, pp. 60–98.

Ivnitski et al., "Biosensors for detection of pathogenic bacteria," *Biosensors & Bioelectronics,* 1999, vol. 14, pp. 599–624.

Cheng et al., "Ultramicroelectrode Ensembles. Comparison of Experimental and Theoretical Responses and Evaluation of Electroanalytical Detection Limits," *Analytical Chemistry,* Apr. 1989, vol. 61, No. 7, pp. 762–766.

Nuzzo et al., "Adsorption of Bifunctional Organic Disulfides on Gold Surfaces," *Journal of American Chemical Society,* 1983, vol. 105, pp. 4481–4483.

O'Sullivan et al., "The Morphology and Mechanism of Formation of Porous Anodic Films on Aluminum," *Proceedings of the Royal Society. Lond,* 1970, vol. 317, pp. 511–543.

Owen, "Market requirements for advanced biosensors in healthcare," *Biosensors & Bioelectronics,* 1994, vol. 9, No. 6, pp. xxix–xxxv.

Sethi, "Transducer aspects of biosensors," *Biosensors & Bioelectronics,* 1994, vol. 9, pp. 243–264.

Ullman, "Formation and Structure of Self–Assembled Monolayers," *Chemical Reviews,* 1996, vol. 96, No. 4, pp. 1533–1554.

Warsinke et al., "Electrochemical immunoassays," *Fresenium J. Anal. Chem.,* 2000, vol. 366, pp. 622–634.

Prior Art

Prior Art

Prior Art

FIG. 7A
FIG. 7B
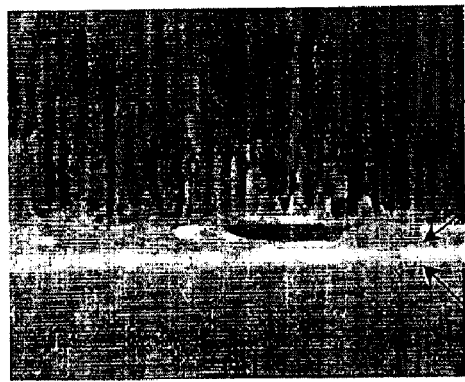
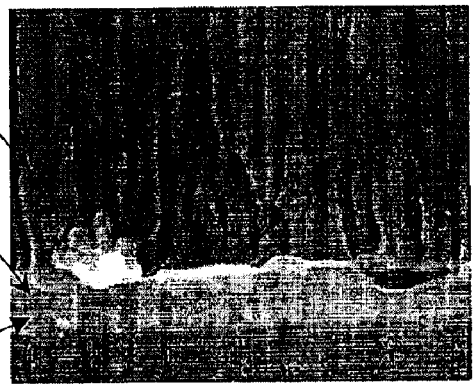

Prior Art

ENABLING NANOSTRUCTURED MATERIALS VIA MULTILAYER THIN FILM PRECURSOR AND APPLICATIONS TO BIOSENSORS

CROSS-REFERENCE TO RELATED APPLICATIONS

This application makes reference to and claims priority to U.S. Provisional Patent Application No. 60/384,386, entitled "Enabling Nanostructured Materials via Multilayer Thin Film Precursor and Applications to Biosensors," filed Jun. 3, 2002. The entire disclosure and contents of the above application is hereby incorporated by reference.

GOVERNMENT INTEREST STATEMENT

This invention is made with government support under contract number ECS97-06873, awarded by the National Science Foundation and contract number DAAH04-95-1-0586, awarded by the United States Department of the Army. The government may have certain rights in this invention.

BACKGROUND OF THE INVENTION

1. Field of the Invention

The present invention relates generally to an anodically generated porous alumina template, and more particularly to a thin-film based multilayer nanoporous template formed on a substrate for the subsequent creation of nanoscale materials.

2. Description of the Prior Art

Anodically generated nanoporous alumina has been widely studied on bulk aluminum substrates and used as a host template for the deposition of a wide variety of materials, see Martin, C. R., Nanomaterials: A membrane-based synthetic approach, Science, 1994, 266 (Dec. 23, 1994): pp. 1961–1965, the entire contents and disclosure of which is hereby incorporated by reference. The work by O'Sullivan and Wood in 1970, see O'Sullivan, J. P. and G. C. Wood, The morphology and mechanism of formation of porous anodic films on aluminum, Proceedings of the Royal Society of London, A., 1970, 317 (1970): pp. 511–543, the entire contents and disclosure of which is hereby incorporated by reference, experimentally examined the role of an applied electric field in steady state pore growth. They proposed that the electric field concentrated at the scalloped inner surfaces of the pore governed pore propagation as well as equilibrium dimensions of pore diameter and barrier layer thickness. This was the first realization that the porous alumina system is dynamic and that the governing parameter ($\Delta V_{applied}$) may be manipulated to achieve the desired porous structure including the pore diameter and barrier layer characteristics. Although dynamic, the porous alumina system was still somewhat limited in application. However, the work of these pioneering researchers (O'Sullivan and Wood) was restricted to bulk aluminum metals and the oxidation/anodization of these bulk aluminum metals, which do not provide any means of eliminating the insulating oxide barrier layer and therefore have limited application for nanowire deposition.

Thus, there is a remaining need to provide a nanoporous, self-assembling, thin-film based template on a substrate with the ability to manipulate the oxide barrier layer in situ, thereby providing a conducting electrode surface at each pore base, with control of the resulting template thickness and pore diameter.

SUMMARY OF THE INVENTION

It is therefore an object of the present invention to provide a thin-film based, multilayer, nanoporous anodic alumina template that will provide for the ability to manipulate and eliminate the oxide barrier layer characteristics of the template.

It is a further object to provide a template that provides a conductive electrode surface created in situ (without the requirement of fragile and tedious template removal and handling) at the pore bases.

It is yet another object to provide a template construct on an arbitrary substrate such that "active" components on the substrate (i.e., integrated silicon based circuitry) may be linked with the nanoporous templated material.

It is yet another object of the present invention to provide a biosensor formed using a multilayer template.

According to a first broad aspect of the present invention, there is provided a means to directly and most efficiently create nanostructures of deposited materials through electrochemical based deposition using, for example, a direct current (DC) galvanostatic method.

According to second broad aspect of the invention, there is provided a suitable diffusion barrier between the anodic alumina template and the underlying electrode layer that may be deposited, for example, by physical vapor deposition and hence converted to its corresponding oxide under anodization.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 5A is a graph showing anodization performance of three thin film systems, while

FIG. 7A shows an anodized Al—Pt bilayer thin film with an unconverted metal layer, while FIG. 7B shows an anodized Al—Pt thin film with barrier layer existence;

DETAILED DESCRIPTION OF THE PREFERRED EMBODIMENT

Figure 1:
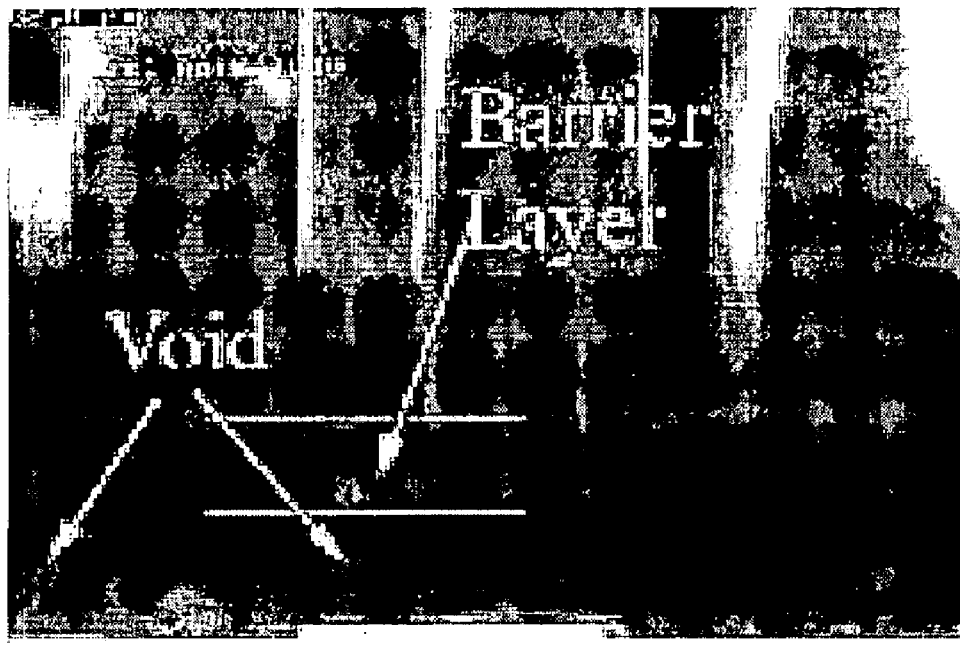
FIG. 1 shows anodized thin film aluminum (Al) on a silicon (Si) substrate.

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term/symbol "95% CI" refers to a 95% Confidence Interval of measured data from anodization instrumentation.

For the purposes of the present invention, the term/symbol "CV" refers to a Cyclic Voltametry electrochemical analysis such as described by Bard and Faulkner, see Bard, A. J. and L. R. Faulkner, Electrochemical Methods: Fundamentals and Applications, Second ed. 2001, New York: John Wiley and Sons, 833, the entire contents and disclosure of which is hereby incorporated by reference.

For the purposes of the present invention, the term/symbol "$d_{pore}$" refers to an anodic alumina pore diameter measured in nanometers (nm).

For the purposes of the present invention, the term/symbol "$d_{SC}$" refers to a space charge region of bulk semiconductor electrodes.

For the purposes of the present invention, the tem/symbol "EHP" refers to electron-hole pairs generated in a semiconductor electrode.

For the purposes of the present invention, the term/symbol "$E_{fsemi}$" refers to a Fermi energy level of a semiconductor electrode.

For the purposes of the present invention, the tern/symbol "$E_{lRedox}$" refers to the electrochemical potential of a Redox reaction as defined by the Nerst Equation by Memming Eq 6.31, see Memming, R., Semiconductor Electrochemistry, 1998, Wiley-V C H: Weinheim, p. 394, the entire contents and disclosure of which is hereby incorporated by reference, as used in the Gerischer Model of charge transfer at electrodes.

For the purposes of the present invention, the term/symbol "$E_{OC}$" refers to an open circuit potential of an electrochemical cell measured by a potentiostat from an anode to a reference electrode.

For the purposes of the present invention, the term/symbol "$j_o^{anod}/j_o^{cath}$" refers to exchange current density of a Redox reaction at open circuit potential at an anode or a cathode measured in miliamps per centimeter squared (mAmps/cm$^2$).

For the purposes of the present invention, the term/symbol "OER" refers to an Oxygen Evolution Reaction occuring at an anode, which is the electrochenicial oxidation of the water molecule to produce dissolved oxygen gas.

For the purposes of the present invention, the term/symbol "$P_{O2ssat}$" refers to supersaturation pressure of dissolved oxygen inside a nanopore measured in Pascals.

For the purposes of the present invention, the term/symbol "$r_{cm}$" refers to a critical nucleation radius of gas phase oxygen bubbles inside a nanopore measured in nanometers (nm).

For the purposes of the present invention, the term/symbol "SHE" refers to a Standard Hydrogen Electrode as described in Bard and Faulkner, see Bard, A. J. and L. R. Faulkner, Electrochemical Methods: Fundamentals and Applications, Second ed. 2001, New York: John Wiley and Sons, 833, the entire contents and disclosure of which is hereby incorporated by reference.

For the purposes of the present invention, the term/symbol "SCE" refers to a Saturated Calomel Electrode as described in Bard and Faulkner, see Bard, A. J. and L. R. Faulkner, Electrochemical Methods: Fundamentals and Applications, Second ed. 2001, New York: John Wiley and Sons, 833, the entire contents and disclosure of which is hereby incorporated by reference.

For the purposes of the present invention, the term/symbol "$T_s$" refers to a substrate temperature during e-beam deposition of metals measured in degrees celsius (° C.).

For the purposes of the present invention, the tern/symbol "$V_s$" refers to a potential barrier due to band bending in a semiconductor electrode.

For the purposes of the present invention, the term/symbol "$\alpha$" refers to a charge transfer coefficient as used in Classical Butler-Volmer kinetics, which indicates the symmetry of the electrochemical reaction energy barrier.

For the purposes of the present invention, the term/symbol "$\Delta\phi_H$" refers to a potential drop in the Helmholtz portion of an electrochemical double layer.

For the purposes of the present invention, the term/symbol "$\Delta\phi_{SC}$" refers to a potential drop in a Space Charge region in a semiconductor electrode.

For the purposes of the present invention, the term/symbol "$\Delta V_{applied}$" refers to applied voltage across an electrochemical cell measured from an anode to a cathode.

For the purposes of the present invention, the term/symbol "$\Delta V_{barrier}$" refers to a potential drop across an alumina barrier layer during anodization.

For the purposes of the present invention, the term/symbol "$\Delta V_{SiO2}$" refers to a potential drop created by the oxidation of a Si substrate.

For the purposes of the present invention, the term/symbol "$\Delta V_{diffusion\ gradient}$" refers to a potential drop created by a concentration overpotential generated by OER, see Vetter, K. J., Electrochemical Kinetics: Theoretical and experimental aspects, 1 ed. Vol. 1, 1967, New York: Academic Press, 789, the entire contents and disclosure of which is hereby incorporated by reference.

For the purposes of the present invention, the term/symbol "$\lambda$" refers to an optimized smoothing parameter for statistical fitting of data described by Moussa and Cheema, see Moussa, M. A. A. and M. Y. Cheema, Non-parametric regression in curve fitting, The Statistician, 1992, 41(1992): p. 209–225, the entire contents and disclosure of which is hereby incorporated by reference.

For the purposes of the present invention, the term/symbol "$\sigma$" refers to the conductivity of an electrolyte as described by Bard and Faulkner, Bard, A. J. and L. R. Faulkner, Electrochemical Methods: Fundamentals and Applications, Second ed. 2001, New York: John Wiley and Sons, 833, the entire contents and disclosure of which is hereby incorporated by reference.

For the purposes of the present invention, the term "biomolecule" refers to nucleic acids, modified RNA, aptamers, proteins, enzymes, polypeptides, including antibodies and fragments thereof, and similar chemical compounds.

For the purposes of the present invention, the term "biorecognition element" refers to any suitable biorecognition element such as an antibody, antigen, enzyme, receptor, ligand, etc. that may be immobilized on a nanostructured substrate of the present invention.

For the purposes of the present invention, the term "anodization" refers to a process whereby the valve metal in question (Al, Ti, Cr, Ta, etc.) is converted to its anodically generated oxide in aqueous acidic solution, typically a diprotic acid such as $H_2SO_4$, oxalic, phosphoric, etc.

For the purposes of the present invention, the term "voltage ramp" refers to a digitally controlled program that increases the applied voltage and therefore the electric field at the appropriate rate to allow for the dissolution of the barrier layer and the breakdown and removal of the metal.

For the purposes of the present invention, the term "substrate" refers to any suitable substrate, such as a sufficiently flat, chemically inert substrate, for example, silicon, glass, mica, quartz, sapphire, polymeric substrates, etc.

For the purposes of the present invention, the term "electrode layer" refers to a layer having the ability to be reduced after anodization of an aluminum layer. Preferable electrode layers of the present invention may be reversibly oxidizable and reducible. Suitable electrode layers include noble metals, platinum, gold, palladium, osmium, rhodium, etc., transparent conducting oxides such as in-doped tin oxide (ITO), etc.

For the purposes of the present invention, the term "valve metal" refers to a metal that produces a stable oxide layer, such as titanium, tantalum, zirconium, niobium, chromium, etc.

Description

Anodically generated nanoporous alumina has been widely studied on bulk aluminum substrates and used as a host template for the deposition of a wide variety of materials, see Martin, C. R., Nanomaterials: A membrane-based synthetic approach, Science, 1994, 266 (Dec. 23, 1994): pp. 1961–1965, the entire contents and disclosure of which is hereby incorporated by reference. The present invention provides for the deposition of a thin film of aluminum precursor onto a substrate. The aluminum thin film may be electrochemically anodized to create the nanoporous alumina template. The thin film template offers important new advantages and presents only minimal new challenges when compared to nanoporous alumina formed on bulk aluminum.

The advantages of the thin film template are the (1) ability to manipulate the barrier layer characteristics as required for the appropriate application; (2) ability to create a conducting electrode surface at the pore base; (3) control of the resulting template thickness; (4) integration of templated nanoscale material with integrated circuit (IC) circuitry; and (5) mechanical support of a fragile thin film alumina template.

Figure 2:
FIG. 2 shows plasma (RIE) etched silicon using alumina as an etching mask.

The present invention provides for the application of a thin film alumina template as a direct pattern transfer mask (FIGS. 1 and 2) for silicon, see Crouse, D. T., et al., Self-ordered pore structure of anodized aluminum on silicon and pattern transfer, Applied Physics Letters, 2000, 76 (January 3): pp. 49–51, the entire contents and disclosure of which is hereby incorporated by reference. As shown in FIG. 1, the alumina barrier layer characteristics at the alumina/silicon interface demonstrate an atypical curvature reversal as compared to bulk systems, thereby producing a void space at the pore centers which were amenable to selective chemical etching with 5 wt % $H_3PO_4$.

This two-step barrier-free template was then used as a mask for reactive ion etching (RIE) of the silicon substrate.

To optimize pore ordering, Masuda developed a silicon-carbon (SiC) nanostamping process that controls the pore nucleation sites thereby improving the regularity and periodicity of the resulting nanoporous structure, Masuda, H., F. Yamada, and M. Satoh, Highly ordered nanochannel-array architecture in anodic alumina, Applied Physics Letters, 1997, 71 (19): p. 2770, the entire contents and disclosure of which is hereby incorporated by reference.

However, a more fundamental problem inherent to the anodization process remains. Under the typical conditions of anodization, an electrically insulating alumina barrier layer exists at the alumina/substrate interface rendering it difficult to directly deposit materials of interest into the pores by the preferred DC electrodeposition mechanism. Several authors have grown the porous alumina layer several microns thick for mechanical stability and then removed the remaining aluminum metal, see Peng, X. S., et al., Synthesis of highly ordered CdSe nanowire arrays embedded in anodic alumina membrane by electrodeposition in ammonia alkaline solution, Chemical Physics Letters, 2001, 343 (2001): pp. 470–474; Xu, D., et al., Preparation and characterization of CdS nanowire arrays by DC electrodeposition in porous anodic aluminum oxide templates, Chemical Physics Letters, 2000, 325 (2000): pp. 340–344; Xu, D., et al., Electrochemical Preparation of CdSe Nanowire Arrays, Journal of Physical Chemistry B, 2000, 104 (21): pp. 5061–5063; and Chen, R., et al., Silver telluride nanowires prepared by DC electrodeposition in porous anodic alumina templates, Journal of Materials Chemistry, 2002, 12 (2002): pp. 2435–2438, the entire contents and disclosures of which are hereby incorporated by reference. The barrier layer at the base of the pores may then be removed with dilute $H_3PO_4$ and a metal of choice is thermally evaporated onto the base of the alumina. However, this tedious and fragile bulk alumina removal technique is not the optimal solution for template based synthesis. Recently, Yang et al. used a simple thin film aluminum-gold (Al—Au) bilayer in an effort to circumvent the need for physically removing the template to achieve elimination of the barrier layer, see Yang, Y., et al., Anodic alumina template on Au/Si substrate and preparation of CdS nanowires, Solid State Communications, 2002, 123 (2002): pp. 279–282, the entire contents and disclosure of which is hereby incorporated by reference.

However, thin film Al—Pt or Al—Au metal bilayers have two primary drawbacks. Firstly, Al—Pt or Al—Au metal systems form intermetallic phases at or near room temperature which catalyze the deleterious oxygen evolution reaction (OER). Secondly, poor mechanical stability and insufficient substrate adhesion of the porous aluminum oxide template may be observed, see Yang, Y., et al., Anodic alumina template on Au/Si substrate and preparation of CdS nanowires, Solid State Communications, 2002, 123 (2002): pp. 279–282, the entire contents and disclosure of which is hereby incorporated by reference, when a thin film of Al is anodized on a base layer of thin film Pt or Au. Therefore, the present invention indicates that the successful creation of a barrier-free, thin film based, nanoporous alumina template requires the introduction of a suitable diffusion barrier between the Al thin film precusor and a Pt underlayer.

The present invention demonstrates the use of an Al—Pt—Si multilayer thin film system with a Ti diffusion barrier for the in situ creation of arrays of platinum nanoelectrodes at the base of the thin film alumina host template. The platinum nanoelectrodes are useful for the DC electrodeposition of a wide variety of metals and semiconductors. The existence of a metallic bottom contact to the electrodeposited nanowires is important for a variety of devices requiring electron transport. A Ti diffusion barrier prevents room temperature formation of intermetallic species and when oxidized to $TiO_2$ provides good substrate adhesion chracteristics between the alumina template and the Pt base electrode. Additionally, the mechanical stability of the Si substrate greatly improves processing and allows the possibility of future integration with IC components.

In a preferred embodiment of the present invention, the Al—Pt—Si substrate systems may be created, for example, by e-beam evaporation followed by anodization in 0.5 M $H_2SO_4$ at 25 v DC. It is not critical to use 0.5 M $H_2SO_4$. A wide range of diprotic acids are suitable for the present invention, such as sulfuric, oxalic, phosphoric acids, etc. The anodization voltage 25 v DC is an exemplary value that is easily changed by one of ordinary skill in the art in light of the teachings of the present invention to create the desired anodic alumina pore diameter. The n-type silicon substrates may be first cut into 15 mm diameter discs from larger wafers with a brass circular bit and diamond paste. The 15 mm diameter wafers may then be RCA cleaned and dipped in a dilute HF solution (1:30 parts water) to remove the native $SiO_2$. The cleaned substrates may then immediately be installed into the vacuum system of the e-beam evaporator.

Four sets of films, with a quantity of 20 per set, were produced for anodization (1) Data Set 1—500 nm Al on a Si substrate, (2) Data Set 2—500 nm Al/40 nm Pt on a Si substrate; (3) Data Set 3—500 nm Al/40 nm Pt on Si with a heated substrate ($T_s$=200° C.) and (4) Data Set 4—500 nm Al/8 nm Ti/40 nm Pt on a Si substrate.

The anodization of the thin aluminum films in particular embodiments of the present invention may be executed in a jacketed glass reaction vessel that allows the electrolyte to be maintained at <5° C. and vigorously agitated. The working electrode assembly exposes only the front metallized surface of the sample to the anodization environment and the voltage may be applied to the backside Al metal contact which is in metal—metal contact with the Pt underlayer via wrap-around lead wires. The anodization conditions may be chosen, for example, from Masuda's work that listed potentiostatic anodization at 25 v DC with 0.5 M $H_2SO_4$ at 10° C. as the empirically determined optimal conditions for self-ordering and pore regularity in $H_2SO_4$, see Masuda, H., F. Hasegwa, and S. Ono, Self-Ordering of cell arrangement of anodic porous alumina formed in sulfuric acid solution, Journal Of Electrochemical Society, 1997, 144 (5): pp. L127–L130, the entire contents and disclosure of which is hereby incorporated by reference. The anodization reaction may be controlled by a digital acquisition system running LabVIEW© which logs the anodization current and controls the applied voltage. During the anodization process, resolution of the current measurement is +/−0.05 mAmps (95% CI) and the voltage measurement resolution is +/−25 mV DC (95% CI) at a data collection frequency of 20 data points per second.

Figure 3:
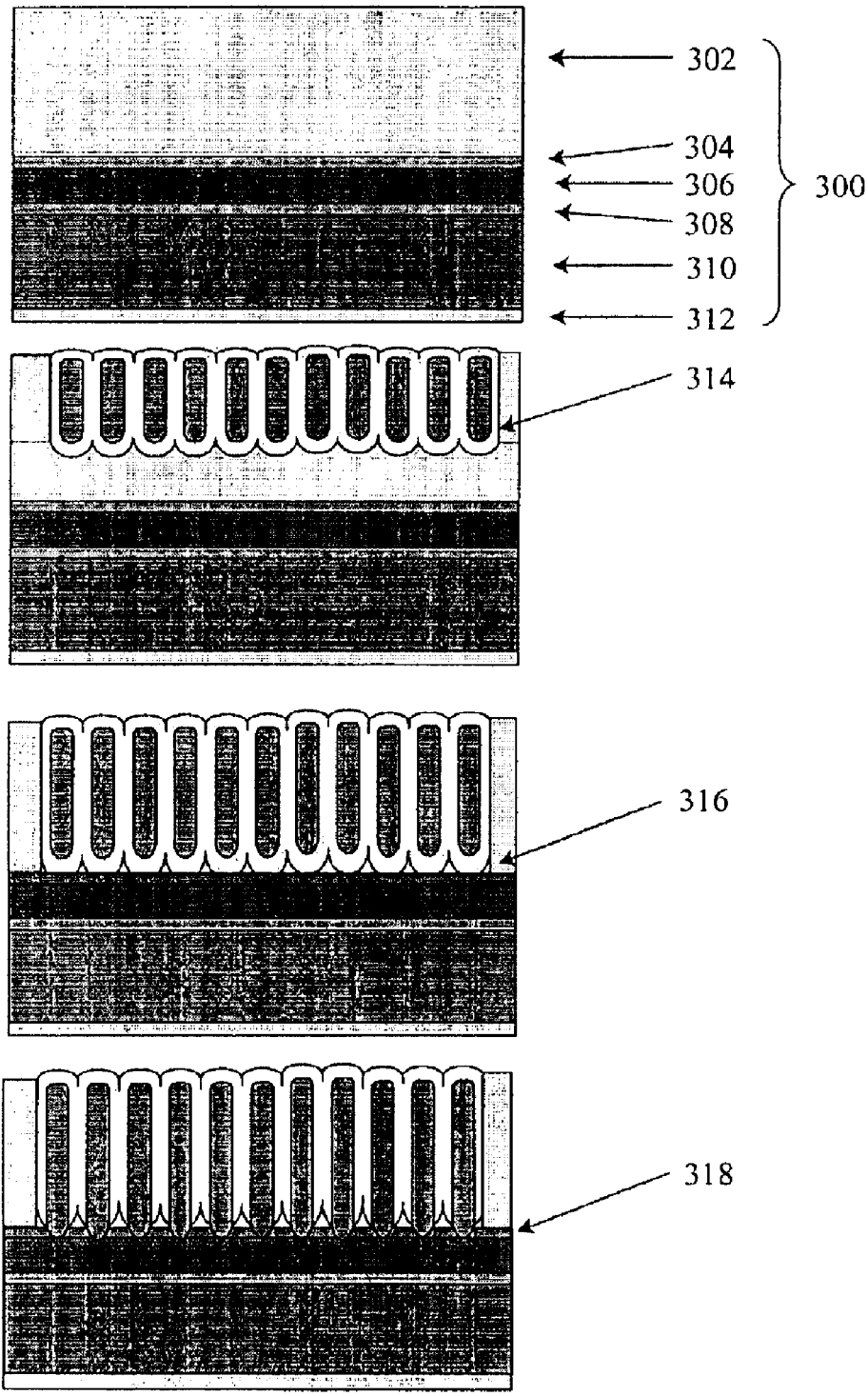
FIG. 3 shows anodization of a multiplayer thin film.

FIG. 3 shows multilayer thin film anodization according to the present invention. Multilayer thin film 300 has an aluminum anodization layer 302, a titanium diffusion barrier 304, a platinum electrode layer 306, a titanium adhesion layer 308, a silicon substrate 310 and an aluminum contact layer 312. During the anodization, advancing pore front 314 may be seen. Pore front 314 terminates at titanium diffusion barrier 304, as shown in element 316, at which time voltage ramping is begun. At element 318, titanium oxide breaks down, platinum catalyzes OER and titanium oxide remains everywhere outside of pore center. The anodization parameters may be precisely controlled to form pore diameters between about 5 to about 200 nm and pore depths are dependent on the amount of aluminum thin film precursor deposited prior to anodization which is ultimately limited by the anodization reaction to approximately 100 μm in depth or less.

A cyclic voltammetry (CV) study established from an electrochemical standpoint the presence or absence of the alumina barrier layer. The CV scans were completed in a similar manner to the work of Serebrennikova, I., P. Vanysek, and V. I. Birss, Characterization of porous aluminum oxide films by metal electrodeposition, Electrochemical Acta, 1997, 42 (1): pp. 145–151, the entire contents and disclosure of which is hereby incorporated by reference. The electrolyte composition was 10 mM silver nitrate in neutral borate buffer (pH=6.7, σ=4.31 mS) with a scan rate of 20 mV/sec. A Gamry electrochemical workstation using a three electrode cell and a SCE reference electrode was used for the study. Three reference CV scans were completed to allow the curves to be interpreted. The first reference CV scan was completed with a 40 nm thin film of Pt on a Si substrate for determination of the location of silver oxidation/stripping and reduction/deposition peaks. The second reference CV scan was completed with nanoporous alumina formed on bulk Al (1 mm thick nominal) to establish the behavior of the barrier layer and demonstrate the absence of the anodic silver stripping peak due to rectification produced by the alumina barrier layer as observed in Serebrennikova, I., P. Vanysek, and V. I. Birss, Characterization of porous aluminum oxide films by metal electrodeposition, Electrochemical Acta, 1997, 42 (1): pp. 145–151, the entire contents and disclosure of which is hereby incorporated by reference. The bulk alumina template was anodized to the equivalent pore depth and diameter for all samples based oil experimentally determined anodization efficiencies. The third reference CV scan was completed with 8 nm Ti deposited on a 40 nm Pt with Si substrate. The thin film Ti on Pt was then converted to anodized $TiO_2$ in 0.5 M $H_2SO_4$. The purpose of the $TiO_2$ CV scan was to establish that the $TiO_2$ semiconductor electrode on Pt with a Si substrate demonstrated both a silver deposition peak and a silver stripping peak. All other CV curves in this application may be interpreted from these three reference curves.

The $TiO_2$-UV light study described herein compared the behavior of the anodically generated $TiO_2$ layer and the behavior of the Pt underlayer to illumination. The UV light generated by a Ushio high pressure mercury lamp with primary spectral lines at 436, 405 and 365 run was used to detect the presence or absence of anodically generated $TiO_2$ as the active electrode material at the base of the pores. The impact of UV light was determined on both the open circuit potential ($E_{OC}$) defined as the equilbrium condition and potentiostatic OER current defined as the kinetic condition. The electrolyte used was borate buffer at 25° C. in a three electrode cell with a silver/silver chloride (Ag/AgCl) reference electrode and a platinum mesh counter electrode. The potentiostatic point for examination of the UV impact on the kinetics of the OER was chosen by determining the onset voltage of the OER using Tafel plots for the various samples. The UV illumination was controlled by a manually operated shutter with a cycle of 60 seconds off/30 seconds on for a total of 6 cycles. Tight control on shutter opening and closing times are not critical to the results.

All micrographs were taken on a Hitachi SE-4500 FESEM with a SEMICAPS digital capture system.

Figure 4:
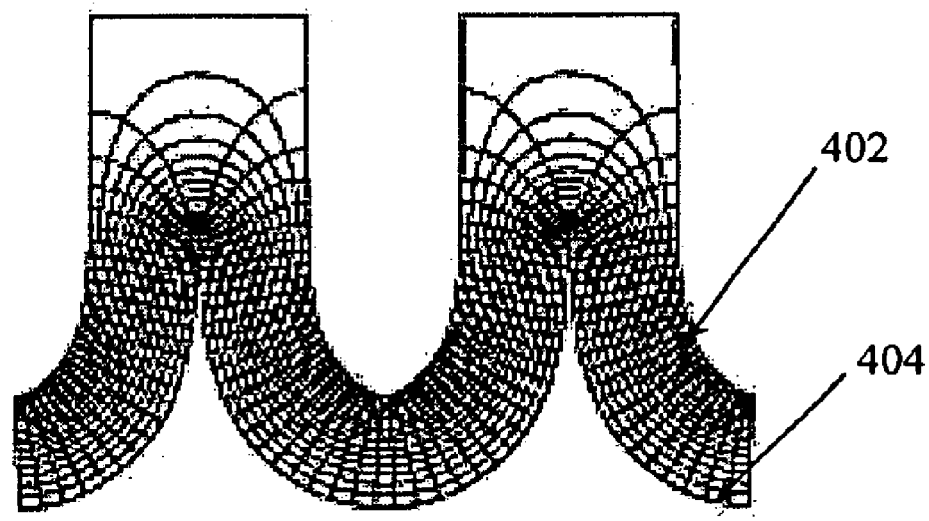
FIG. 4 shows electric field lines for bulk aluminum under steady state pore growth with a concentration of the field at the interior scalloped interface-creating field enhanced dissolution.

The utility of thin film metal underlayers for anodization of aluminum thin films has been recently demonstrated using tantalum (Ta) by Vorobyova and Outkina, see Vorobyova, A. I. and E. A. Outkina, Study of pillar microstructure formation with anodic oxides, Thin Solid Films, 1998, 1–2 (Jul. 1, 1998): pp. 324, the entire contents and disclosure of which is hereby incorporated by reference, and titanium by Tatarenko and Solntsev, see Tatarenko, N. I., V. A. Solntseva, and A. N. Rodionov, Novel nanoscale field emission structures: Fabrication technology, experimental and calculated characteristics, Journal of Vacuum Science and Technology B, 1999, 17 (2): pp. 647–654, the entire contents and disclosure of which is hereby incorporated by reference. Vorobyova and Outkina created a thin film Al—Ta bilayer by evaporating 300 nm Al on 50 nm tantalum (Ta) with a Si substrate. The Al layer was then: potentiostatically anodized in oxalic acid at 30 v DC. The structure of the alumina/$Ta_2O_5$ interface upon termination of the Al anodization reaction and subsequent voltage ramping showed interesting results. The barrier layer of the alumina is shown to electrochemically etch to completion leaving the alumina pores open to the $Ta_2O_5$ layer. The mechanism that etches the alumina barrier layer is the same electric field assisted dissolution process (FIG. 4) that allows steady state pore propagation in bulk Al anodization, see Thamida, S. K. and H. C. Chang, Nanoscale pore formation dynamics during aluminum anodization, Chaos, 2002, 12 (1): pp. 240–251, the entire contents and disclosure of which is hereby incorporated by reference. In FIG. 4, element 402 defines the oxide/electrolyte interface and element 404 defines the metal/oxide interface. Increasing the applied electric field across the alumina barrier layer via ramping the anodization voltage and simultaneously exhausting the supply of Al allows the dissolving oxide/electrolyte interface to approach the metal/oxide interface and ultimately eliminate the oxide barrier layer. The use of solitary Ta or Ti underlayers has a significant limitation for the present invention due to the fact that anodic tantalum pentoxide ($Ta_2O_5$) and anodic titanium oxide ($TiO_2$) are relatively wide band gap semiconductors ($E_g$=4.3 eV and 3.1 eV, respectively) and therefore a relatively poor electrode material for subsequent electrochemical deposition into the nanoporous template. Platinum is widely regarded as having optimal electrode characteristics for electrochemical deposition of a wide variety of metals and semiconductors. Additionally, platinum electrodes and platinum oxidation are well studied in the literature, see Conway, B. E., Electrochemical oxide film formation at noble metals as a surface-chemical process, Progress in Surface Science, 1995, 49 (4): pp. 331–452, the entire contents and disclosure of which is hereby incorporated by reference. The oxidation of Pt to form platinum oxides has been demonstrated to quickly create a 2-D oxide layer which slowly uses a place exhange mechanism to form a true 3-D bulk oxide phase. Platinum oxides formed on Pt thin films have been demonstrated by a variety of researchers in the field to be reduced in acid environments common to aluminum anodization, see Tremiliosifilho, G., G. Jerkiewicz, and B. E. Conway, Characterization and significance of the sequence of stages of oxide film formation at Platinum generated by strong anodic polarization, Langmuir, 1992, 8 (2): pp. 658–667, the entire contents and disclosure of which is hereby incorporated by reference. However, use of Pt thin film electrodes in aqueous systems at high anodic potentials (exceeding 1.23 V vs. SHIE in acidic solutions) may be accompanied by a vigorous and undesirable OER. Therefore, use of platinum or other suitable metal as an underlayer in thin film anodization of aluminum to create a nanoporous alumina template with in situ removal of the barrier layer and avoiding or minimizing the subsequent OER through the use of a diffusion barrier is further discussed in the present invention.

Anodization behavior of thin film Al—Pt bilayers on Si substrate: The curves illustrated in FIGS. 5A and 5B demonstrate the typical anodization performance of three types of thin film systems discussed in the present invention. The curve labelled "Al on Si" represents the anodization behavior of 500 nm Al directly on a Si substrate (Data Set 1). The curve labelled "Al—Pt on Si" represents the performance of 500 nm Al with a Pt underlayer on a Si substrate (Data Set 2). The curve labelled "Multilayer on Si" illustrates the performance of a multilayer template (Data Set 4). The curve labeled "Voltage Ramp" illustrates the applied voltage program for the anodization and is plotted against the second y-axis. For simplicity, the graph has been normalized to allow the anodization performance of the various thin film systems to be compared by inspection. The normalization of time was done by assigning the endpoint time of the various anodizations and scaling the elapsed anodization time by this endpoint. Anodization current was normalized by assigning the maximum current achieved before the anodization endpoint time and scaling all current values relative to this maximum anodization current.

Figure 6:
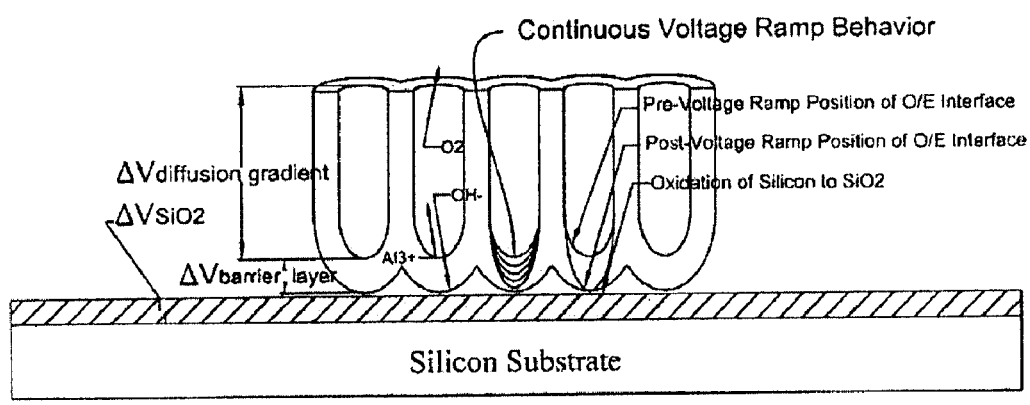
FIG. 6 is a schematic of thin film porous alumina highlighting critical voltage drops with the central pore illustrating continuous movement of O/E interface upon applied voltage ramping.

The Al on Si system (Data Set 1) matches the published reports for bulk Al anodization with an initial drop in the current with normalized time<0.25, indicating the formation of a planar surface oxide layer at early anodization stages. This is followed by an increase in the current as pore nucleation begins with subsequent steady state pore growth. At the anodization endpoint, corresponding to normalized time=1, the Al thin film is completely consumed and the Si substrate at the interface becomes quickly converted to $SiO_2$. It is instructive to examine the primary sources of voltage drop in this system as shown by FIG. 6. Initially the voltage drop is largely across the scalloped alumina barrier layer during steady state pore growth ($\Delta V_{barrier}$). As the propagating interface approaches the silicon surface, the $O^{2-}$ and $OH^-$ ions begin converting the Si to $SiO_2$. The current quickly decays to zero when the magnitude of the applied voltage approaches $\Delta V_{SiO2}$, i.e. the voltage drop due to the growing $SiO_2$ layer. The alumina barrier layer is observed in FESEM images to be present and may be either concave or convex depending on the anodization conditions and corresponding electric field as described by Thamida, S. K. and H. C. Chang, Nanoscale pore formation dynamics during aluminum anodization, Chaos, 2002, 12 (1): pp. 240–251, the entire contents and disclosure of which is hereby incorporated by reference.

In contrast, the Al—Pt on Si system (Data Set 2) illustrates substantially different behavior. The characteristic current dip indicative of the formation of a planar surface oxide layer is absent. Additionally, the pore initiation point is not clearly observable as in the Al—Si system. The behavior of anodization current as the pore front nears the Pt interface differs remarkably as well. For the Al—Pt on Si system prepared at ambient temperature in the e-beam evaporator, the current increases sharply as the propagating pore front nears the platinum interface. However, the sharp rise in current has been shown by FESEM examination not to corrolate with the endpoint of the aluminum anodization but rather to the acceleration of the OER. Ten anodized Al—Pt bilayers on Si substrates were immediately stopped after the sharp increase in recorded anodization current (FIGS. 7A and 7B). In FIGS. 7A and 7B, layer 702 is alumina, layer 704 is Al—Pt and layer 706 is platinum. Typically, a layer of unconverted metal approximately 30 nm thick was observed by FESEM between the advancing pore front and the platinum underlayer.

The unconverted layer highlighted in FIGS. 7A and 7B is an indication of an amorphous Al—Pt intermetallic system which may exist at compositions between 60–75 atomic % Al. The Al—Pt reaction was first investigated by Comer, see Comer, J. J., Electron diffraction data on new compounds in the system platinum-aluminum, Acta Crystallographica, 1964, 17: pp. 444–445, the entire contents and disclosure of which is hereby incorporated by reference, and Murarka, see Murarka, S. P., I. A. Blech, and H. J. Levinstein, Thin-film interaction in aluminum and platinum, Journal of Applied Physics, 1976, 47 (12), the entire contents and disclosure of which is hereby incorporated by reference. They found that Al—Pt reacted rapidly near 250° C. to form a variety of intermetallic species with the most stable of these being $Al_2Pt_3$. Colgan et al., see Colgan, E. G., A review of thin film aluminide formation, Material Science Reports, 1990, 5 (1990): pp. 1–44; Colgan, E. G., C. Y. Li, and J. W. Mayer, Interfacial reaction-induced morphological instabilities in thin Al/Pt and Al/Pd films, Journal of Materials Research, 1987, 2 (5): pp. 557–567; and Colgan, E. G., C. Y. Li, and J. W. Mayer, Void formation in thin Al films, Applied Physics Letters, 1987, 51 (6): pp. 424–426, the entire contents and disclosures of which are hereby incorporated by reference, and more recently Radi, see Radi, Z. and P. B. Barna, Detailed model on the amorphous Al—Pt phase growth in thin film systems, Surface Coatings and Technology, 1998, 100–101 (1998): pp. 90–93; Radi, Z., P. B. Barna, and J. Labar, Kirkendall voids and the formation of amorphous phase in the Al—Pt thin film system prepared by high temperature successive deposition, Journal of Applied Physics, 1996, 79 (8): pp. 4096–4100; and Radi, Z., J. Labar, and P. B. Barna, Diffusion coefficient of Al in metastable, amorphous Al—Pt phase, Applied Physics Letters, 1998, 73 (22): pp. 3220–3222, the entire contents and disclosures of which are hereby incorporated by reference, examined the formation of voids in e-beam deposited Al—Pt bilayers. Radi states the Al—Pt reaction proceeded by first forming an initial layer of an amorphous Al—Pt intermetallic followed by a crystalline $Al_2Pt_3$ compound at substrate temperatures exceeding 120° C. Since Al has been determined to be the fast diffusing component in the Al—Pt system, the characteristic voids, i.e. Kirkendall voids, see Radi, Z., P. B. Barna, and J. Labar, Kirkendall voids and the formation of amorphous phase in the Al—Pt thin film system prepared by high temperature successive deposition, Journal of Applied Physics, 1996, 79 (8): pp. 4096–4100, the entire contents and disclosure of which is hereby incorporated by reference, may be observed in the aluminum layer immediately adjacent to the growing intermetallic system. The rapid growth of these voids indicates that the source of Al diffusion is preferentially the void surface, transported by the facile surface diffusion mechanism. The ambient substrate temperature used in embodiments of the present invention was estimated to achieve temperatures between 100–150° C. during condensation of metals onto the Si substrate, thereby creating the Al—Pt intermetallics at the interface and the observed void layers.

Figure 8:
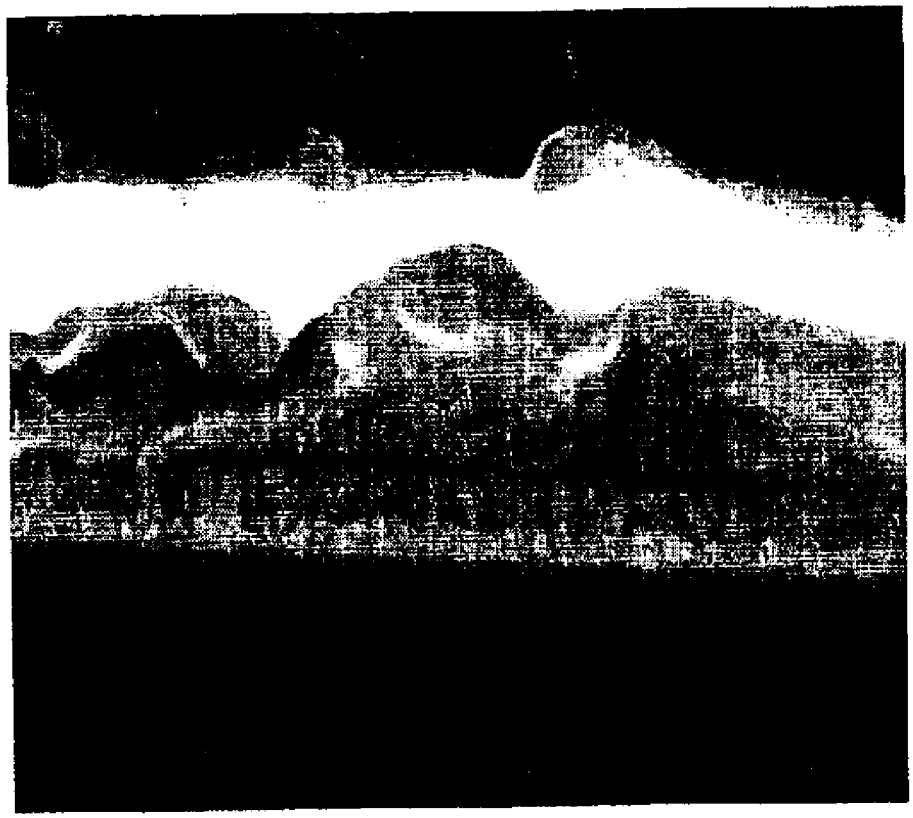
FIG. 8 shows Al—Pt on Si with a substrate temperature of 200° C. showing contrast among the Al layer, Al—Pt layer, and Pt layer.
Figure 9:
FIG. 9 shows anodized Al—Pt on Si with a substrate temperature of 200° C. showing existence of barrier layer and that anodization stopped at the current jump.
Figure 10:
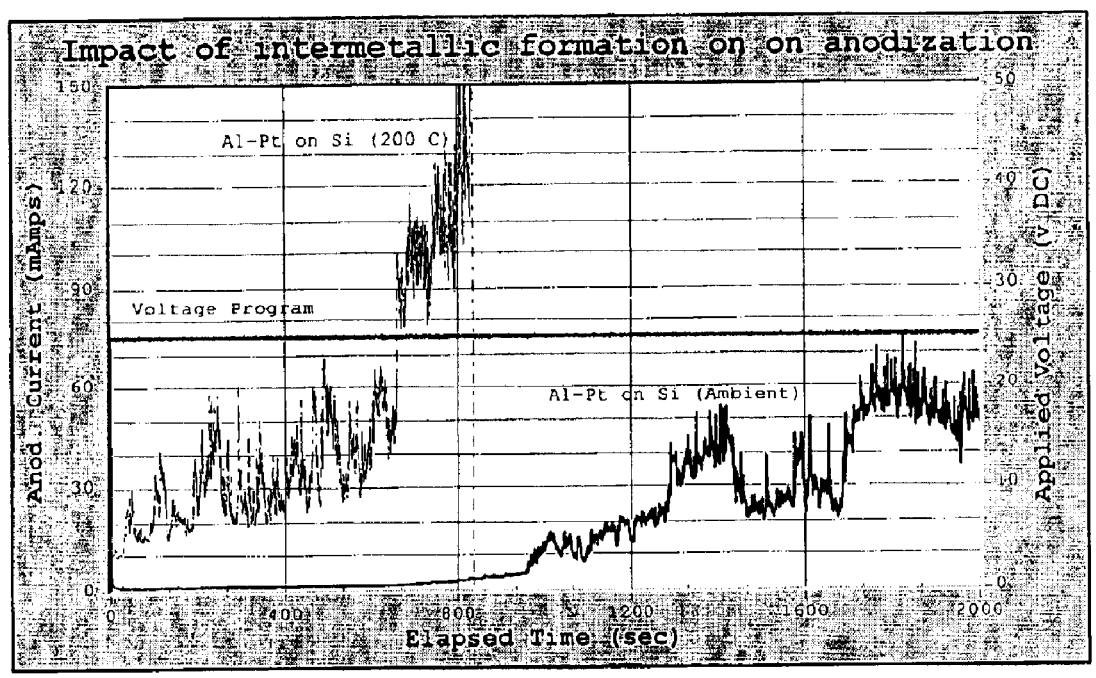
FIG. 10 shows anodization performance of Al—Pt on Si with 2 substrate temps, with Data Set 2 showing Al—Pt on Si: 500 nm/40 nm Pt on Si with an ambient substrate temperature, and Data Set 3 showing Al—Pt on Si: 500 nm/40 nm Pt on Si with a 200° C. substrate temperature.

In order to illustrate the impact of Al—Pt intermetallics on the anodization of thin film aluminum, an Al—Pt bilayer (Data Set 3) was deposited with the Si substrate heated to 200° C., which significantly enhanced the formation of the intermetallics and the voids in the aluminum layer. FIG. 8 shows three distinct metal layers: 25 nm Pt layer, 40 mm Al—Pt intermetallic layer, and 150 run Al layer on silicon. FIG. 9 illustrates the pore system that developed during the anodization. The contrasting anodization behavior of Data Sets 2 and 3 are shown in FIG. 10.

Both the micrographs and the anodization behavior of Data Sets 2 and 3 support the conclusion that Al—Pt intermetallics formed by physical vapor deposition of Al—Pt bilayers at either ambient temperature or 200° C. enhance the OER and mask the anodization endpoint of the aluminum. However, if the anodization and OER is allowed to proceed well past the large current jump observed at 2000 seconds elapsed time, an anodization endpoint may be identified: using signal processing techniques. The FESEM examination of these extended anodization samples showed two critical features: existence of an oxide barrier layer and a misshapen porous structure at the alumina-Pt interface due to the Al—Pt intermetallic region.

The existence of the barrier layer at the interface after the anodization endpoint for Al—Pt thin films may be explained by examining the location of the most significant voltage drops. During the steady state pore propagation far from the Pt interface, the primary voltage drop in the system is developed across the alumina barrier layer ($\Delta V_{barrier}$) as shown in FIG. 6. As the propagating pore front approaches the Pt interface, the observed current becomes divided between the Al anodization reaction and the OER. Initially the voltage drop associated with the OER and subsequent diffusion of participant species ($\Delta V_{diffusion\ gradient}$) is approximately two orders of magnitude lower than $\Delta V_{barrier}$. A large peak in the current may be observed, as Pt rich sites within the intermetallic region become electrical conduction paths in the oxidized/anodized Al—Pt intermetallic system. This reduction in $\Delta V_{barrier}$ produces two effects. Firstly, the reduced $\Delta V_{barrier}$ slows the rate of aluminum anodization and attempts to reduce the radius of curvature of the propagating pore base. Secondly, the remaining applied voltage enables a vigorous OER developing a diffusion gradient of participant species within the pore. The OER continues to accelerate within the intermetallic region due to more Pt sites becoming available as anodization of the Al—Pt intermetallic continues. Hence, the concentration overpotential for this reaction initially increases sharply followed by a slower stabilization to an equilibrium value. Ultimately, the observed current is distributed between the field limited Al anodization reaction and the diffusion limited OER. This significantly slows the rate of pore propagation towards the platinum interface. The alumina barrier layer remains in place due to this distribution of current and the inability to produce the necessary electric field strength to continue field assisted dissolution at the oxide/electrolyte interface regardless of subsequent applied voltage ramping.

A high degree of supersaturation of dissolved oxygen in the nanopore results from the accelerated OER occurring at Pt rich sites within the intermetallic region. According to Yang, Y., et al, Anodic alumina template on Au/Si substrate and preparation of CdS nanowires, Solid State Communications, 2002, 123 (2002): pp. 279–282, the entire contents and disclosure of which is hereby incorporated by reference, the nucleation of oxygen bubbles inside the nanopore produces a subsequent decline of the OER rate due to the pores filling with oxygen bubbles. However, this effect has not been observed in the present invention. In fact, the small radii of the nanopores (10 nm) is below the experimentally determined critical nucleation radius of 35 nm in 10 $\mu$m diameter silica glass capillaries where the applied oxygen supersaturation pressure was 15 MPa as determined by Brereton, G. J., R. J. Crilly, and J. R. Spears, Nucleation in small capillary tubes, Chemical Physics, 1998, 230 (1998): pp. 253–265, the entire contents and disclosure of which is hereby incorporated by reference. The threshold of heterogeneous nucleation as measured by the oxygen supersaturation pressure was found to have the following relationship:

$$\log(P_{o_{2,sat}}) \propto 1/\sqrt{d_{pore}}.$$

Thus, as a first approximation for $r_{crit}$ approaching the pore radius (10 nm), the supersaturation pressure of oxygen in the nanopore may be estimated to be on the order of 160 MPa. This high pressure would be very difficult to achieve inside the pore with no imposed hydrodynamic flow except diffusional flow. Therefore, the most likely scenario is that the OER occurs at the base of the pore with diffusional flow of supersaturated oxygen along the length of the pore and subsequent bubble nucleation at the pore exit. The bubbles of oxygen continue to grow until body forces of the bubble overcome the attraction to the alumina surface and detach. Thus, cyclically interrupting current paths on the electrode and changing the effective surface area creates the observed noise in the current.

Development of the multilayer thin film system: It is clear that simple Al—Pt bilayers will not produce the desired nanoporous template. Therefore a multilayer thin film system on Si substrate has been provided by the present invention comprising at least three layers. The first layer is the Pt underlayer that serves as the "active" electrode for subsequent DC electrodeposition of materials into the nanopore. The second layer is a thin Film "valve metal" (e.g., Ta, Ti, niobium (Nb), zirconium (Zr)) that serves as a diffusion barrier between the Pt underlayer and the Al top layer. The top-most layer is e-beam deposited as Al and later converted via anodization to the nanoporous alumina. The "valve metal" diffusion barrier preferably has the following characteristics, (1) the ability to deposit the barrier material of choice in the same physical vapor deposition device as Al and Pt layers, (2) limited intermetallic formation with Al and Pt layers at ambient substrate temps with good mechanical adhesion characteristics, (3) an anodization product of the barrier layer material that is stable and may selectively be removed at the pore centers by an in situ technique, and (4) an anodization product of the barrier layer preferably supresses the OER to allow field driven barrier layer removal of alumina at pore bases.

The present invention provides an in situ approach to forming a multilayer thin film based nanoporous alumina template by inducing the selective removal of a barrier layer, particularly by an avalanche breakdown mechanism created by the ramping of the applied voltage. This removes the barrier layer materials only at the base of the alumina pores and leaves the remaining material intact, hence exposing the underlying electrode layer for further use. This electrode has the characteristic that it may immediately participate in electrochemical deposition reactions without the requirement of further processing.

The present invention also provides control of the barrier layer characteristics of the alumina via controlling, or minimizing, the OER reaction during anodization and hence the electric field at the base of the pores. The OER reaction may be controlled by using a suitable diffusion layer.

Figure 11:
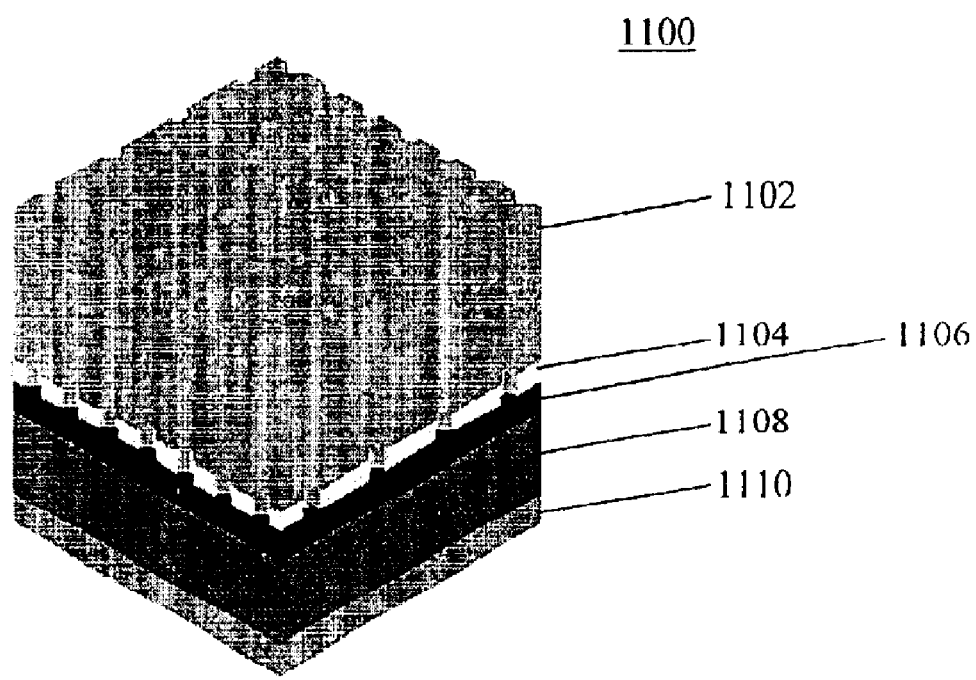
FIG. 11 shows a cross-section of a multilayer thin film template according to the present invention with a Pt electrode surface shown at the base of the pores.

A preferable diffusion barrier for the present invention is Ti, which has been shown by the present invention to achieve all four requirements. A schematic of the multilayer thin film system with a Ti barrier layer after aluminum anodization and subsequent voltage ramping is shown in FIG. 11. Multilayer thin film system 1100 comprises alumina layer 1102, $TiO_2$ layer 1104, Pt layer 1106, Si substrate 1108, and Al contact layer 1110.

Pt—Ti thin film bilayers have been examined for application as electrodes for non-volatile ferroelectric RAM devices, see Hwang, Y. S., et al., The effect of Al/Pt interface reaction on lead-zirconate-titanate capacitor and the optimization of via contact for double metal ferroelectric RAM, Japanese Journal of Applied Physics: Part 1, 1998, 37 (3 B): pp. 1332–1335, the entire contents and disclosure of which is hereby incorporated by reference. According to the Pt—Ti phase diagram the following phases may exist: PtTi, $Pt_8Ti$, $Pt_3Ti$ and γ-phase PtTi, see Murray, J. L., The Pt—Ti binary phase diagram-ASM Handbook, Binary Alloy Phase Diagrams, 1982, 2: pp. 1915–1916, the entire contents and disclosure of which is hereby incorporated by reference. However Lee et al. found only the PtTi phase in existence in thin film bilayer systems, see Lee, C. K., C. D. Hsieh, and B. H. Tseng, Effects of titanium interlayer on the formation of platinum silicides, Thin Solid Films, 1997, 303 (1997): pp. 232–237, the entire contents and disclosure of which is hereby incorporated by reference. The formation temperature of the PtTi phase is reported to the approximately 500° C. by Park, K. H., et al., Microstructures and interdiffusion of Pt/Ti electrodes with respect to annealing in oxygen ambient, Journal of Materials Research, 1995, 10 (7): pp. 1790–1794, the entire contents and disclosure of which is hereby incorporated by reference. Kweon examined the interdiffusion of Ti into Pt and resulting hillock formation in sputtered Pt—Ti films, see Kweon, S. Y., et al., Platinum hillocks in Pt—Ti film stacks deposited on thermally oxidized Si substrate, Japanese Journal of Applied Physics: Part 1, 2001, 40 (2001): pp. 5850–5855, the entire contents and disclosure of which is hereby incorporated by reference. Kweon reports that as-deposited samples (200 nm Pt/20 nm Ti on Si) with a substrate temperature of 500° C. showed no measurable intermixing as determined by Auger Electron Spectroscopy (AES). In fact, the bilayers are typically annealed at 400° C. for 30 additional minutes before a measurable amount of diffused Ti is found in the Pt layer. In addition, Al—Ti thin film systems have been examined for the reduction of electromigration of Al in integrated circuit metallizatons. Of the possible Al—Ti compounds, $Al_3Ti$ is the most thermodynamically stable, $T_f$=350° C., and is most often observed in thin film bilayers as reported by Colgan, E. G. and J. W. Mayer, Thin-film reactions of Al with Co, Cr, Mo, Ta, Ti and W, Journal of Materials Research, 1989, 4 (4): pp. 815–820; and Colgan, E. G., A review of thin film aluminide formation, Material Science Reports, 1990, 5 (1990): pp. 1–44, the entire contents and disclosures of which are hereby incorporated by reference. Aluminum is the fast diffusing species of the couple and at substrate temps<150° C. the relatively slow diffusion of Al will preferentially occur along Ti grain boundaries and thereby reduce the rate of Al—Pt intermetallic formation compared to a bulk Al—Pt interface. Therefore, the literature on Pt—Ti and Al—Ti bilayers is consistent with its use as a diffusion barrier for the Al—Pt thin film depositions.

Of the possible candidate valve metals, metals such as Ti and Ta are preferable to deposit by e-beam evaporation. For example, tantalum has been shown to significantly suppress the OER during anodization, see Laleko, V. L., L. L. Odynets, and T. L. Voitenko, Electrical conductivity of anodic tantalum oxide films in contact with al electrolyte, Russian Journal of Electrochemistry, 1994, 30 (6): pp. 718–719, the entire contents and disclosure of which is hereby incorporated by reference. However, the effective band gap of anodically formed tantalum oxide is 4.3 eV vs. 3.2 eV for anodic titanium oxide, see Schultze, J. W. and M. M. Lohrengel, Stability, reactivity and breakdown of passive films. Problems of recent and future research, Electrochimica Acta, 2000, 45 (2000): pp. 2499–2513, the entire contents and disclosure of which is hereby incorporated by reference. Therefore, it requires significantly more applied voltage to achieve the threshold current for mechanical and electrical breakdown of tantalum oxide. Due to power supply limitations, the lower voltage breakdown characteristics of titanium are preferred for the present invention. Using Sul's results for sulfuric acid, see Sul, Y. T., et al., The electrochemical oxide growth behavior on titanium in acid and alkaline electrolytes, Medical and Engineering Physics, 2001, 23 (2001): pp. 329–346, the entire contents and disclosure of which is hereby incorporated by reference, the required anodization voltage for complete conversion of the deposited thin film Ti layer is approximately 8 v DC with an anodization rate of 20 nm/sec. Hence the anodization of the 8 nm Ti thin film to a 16 nm anodically generated titanium oxide layer is easily accomplished by the Al anodization potential of 25 v DC in under a second.

Figure 5A:
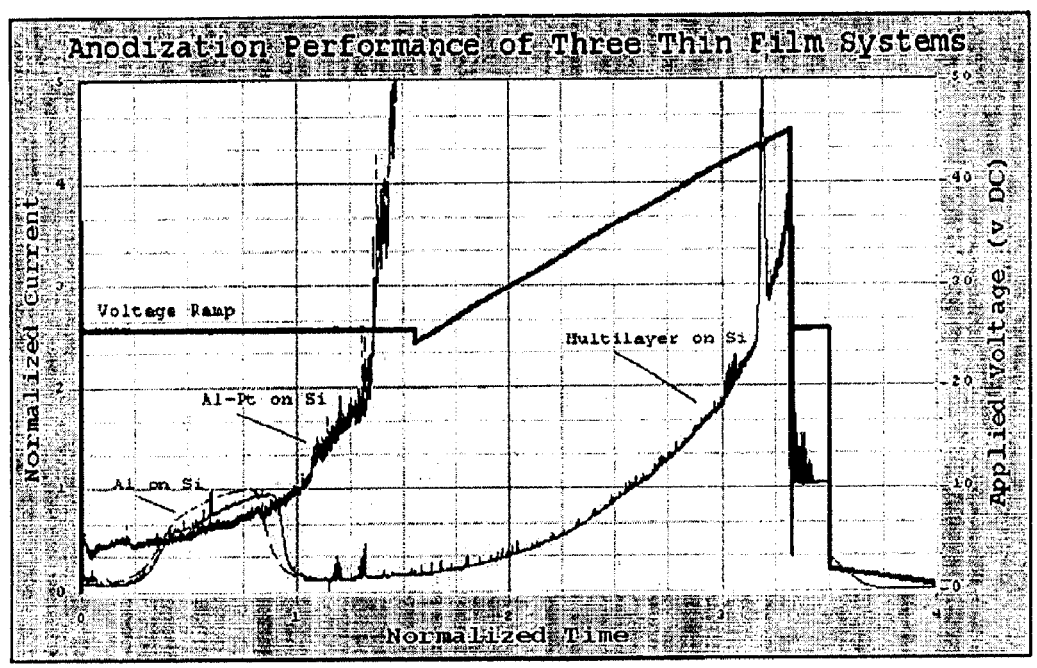
Figure 5B:
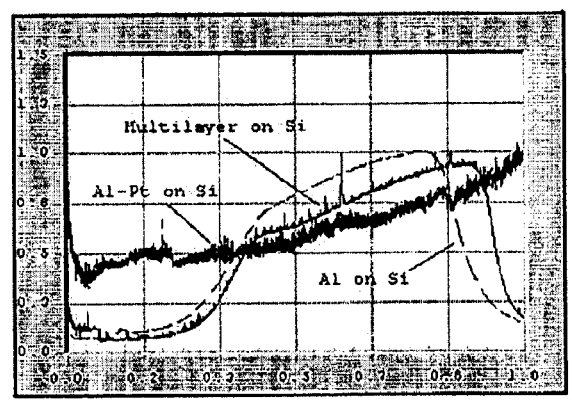
FIG. 5B is a graph showing an expanded portion of the graph of FIG. 5A, with Data Set 1 showing Si: 500 nm on Si, Data Set 2 showing Al—Pt on Si: 500 nm/40 nm platinum (Pt) on Si, and Data Set 4 showing a multiplayer template: 500 nm Al/8 nm titanium (Ti)/40 nm Pt on Si.

The anodization endpoint is clearly visible in FIGS. 5A and 5B for the sample labeled "Multilayer on Si" with a sharp decline in reaction current at the normalized endpoint value. This mullltilayer sample demonstrates a major processing improvement with a post-anodization OER current of less than 2 mAmps/$cm^2$. Therefore the applied voltage ramp increases the electric field across both the titanium oxide and the alumina barrier layer without creating a large increase in the concentration overpotential inside the pore associated with the OER ($\Delta V_{diffusion\ gradient}$). According to Thamida, S. K. and H. C. Chang, Nanoscale pore formation dynamics during aluminum anodization, Chaos, 2002, 12 (1): pp. 240–251, the entire contents and disclosure of which is hereby incorporated by reference, the mechanism of alumina pore development is described as a coupled moving boundary problem where the local electric field strengths found across the alumina barrier layer dictate the movement of the oxide/electrolyte interface and the metal/oxide interface. The oxide/electrolyte interface dissolves the alumina formed at the metal/oxide interface due to the field focusing effect of the scalloped shaped pore front during steady state propagation. Therefore, if the supply of aluminum is consumed, the metal/oxide interface propagation may terminate and the oxide/electrolyte interface may stay at equilibrium thickness at a constant applied field. By ramping the voltage, the applied electric field across the alumina barrier layer may be increased to allow continued dissolution and movement of the oxide/electrolyte interface towards the stationary metal/oxide interface as shown in FIG. 6. Thus, the alumina barrier layer is removed incrementally during the voltage ramp. This has been verified experimentally by FESEM examination of ramped vs. non-ramped samples. Likewise, Voroboyova found similar voltage ramping requirements for barrier layer removal with tantalum oxide pillars, see Vorobyova, A. I. and E. A. Outkina, Study of pillar microstructure formation with anodic oxides, Thin Solid Films, 1998, 1–2 (Jul. 1, 1998): p. 324, the entire contents and disclosure of which is hereby incorporated by reference, and Tatarenko with titanium oxide pillars, see Tatarenko, N. I., V. A. Solntseva, and A. N. Rodionov, Novel nanoscale field emission structures: Fabrication technology, experimental and calculated characteristics, Journal of Vacuum Science and Technology B, 1999, 17 (2): pp. 647–654, the entire contents and disclosure of which is hereby incorporated by reference.

Figure 12:
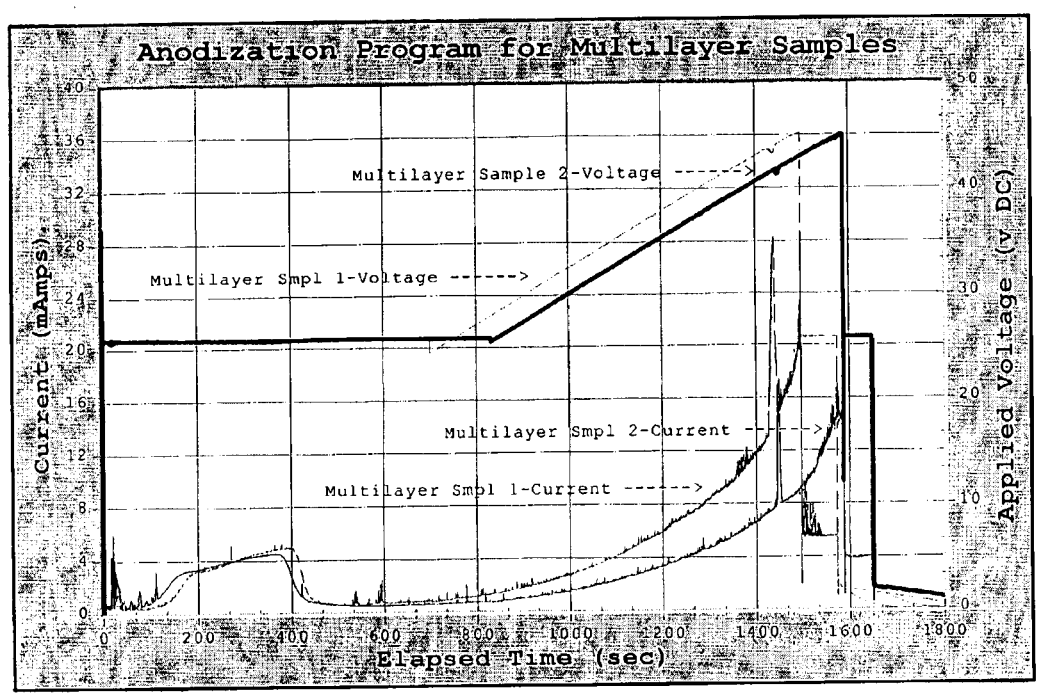
FIG. 12 shows anodization and breakdown behavior of a multilayer thin film system, with Data Set 4 showing a multiplayer template: 500 nm Al/8 nm Ti/40 nm Pt on Si.
Figure 13:
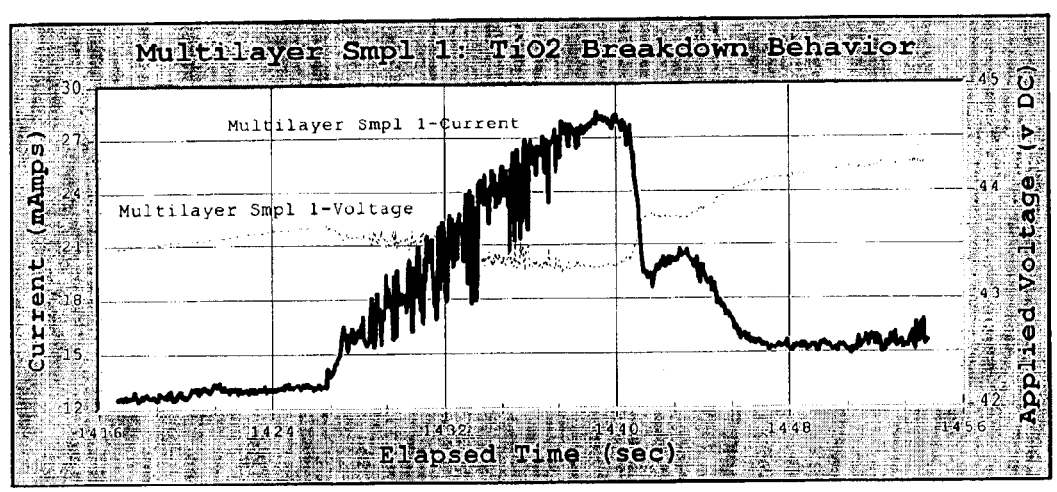
FIG. 13 shows multilayer Ti oxide breakdown characteristics, with Data Set 4 showing a multiplayer template: 500 nm Al(8 nm Ti/40 nm Pt on Si.
Figure 18:
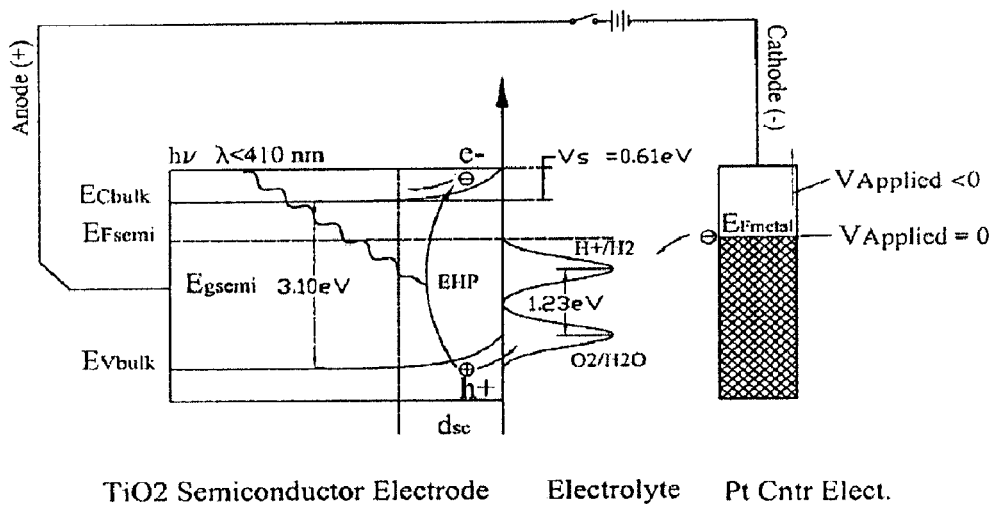
FIG. 18 shows a $TiO_2$ semiconductor electrode with Gerischer Model energy states in electrolyte under dark/short circuit conditions.

As the pore front approaches the Ti layer, the migration of $O^{2-}$ and $OH^-$ ions through the alumina barrier layer anodizes the Ti thin film. The anodization product of titanium with the previously stated anodization conditions has been shown by Delplancke, J. L. and R. Winand, Galvanostatic anodization of Titanium-I, Structures and compositions of the anodic films, Electrochimica Acta, 1988, 33 (11): pp. 1539–1549, the entire contents and disclosure of which is hereby incorporated by reference, to produce largely crystalline $TiO_2$ in both anatase and rutile phases. The removal of $TiO_2$ from the platinum electrode follows a modified anodic breakdown mechanism. The vast literature on the subject of anodic breakdown of oxides during anodization assumes the effective electric field is constant within the oxide. Additionally, the growing oxide thickness and the flux of ionic species are critical parameters in the breakdown process. An important aspect of the anodic breakdown is the injection of current from the electrolyte via the redox reaction occurring at the oxide/electrolyte interface. In the present invention, the redox reaction providing current injection is the OER. In contrast, metal-insulator-metal structures have a constant oxide thickness and the voltage is ramped producing an increase in the applied electric field. Hence, the titanium oxide layer behavior in the present invention may be described as a combination of these previously studied oxide systems with an electrolyte electrode, a fixed titanium oxide thickness, a redox reaction at the oxide/electrolyte interface and the ramping of the applied electric field. As stated by Tsuda, N., et al., Electronic Conduction in Oxides, Springer Series in Solid-State Sciences, ed. M. Cardona and P. Fulde, Vol. 94, 1991, Berlin: Springer-Verlag, the entire contents and disclosure of which is hereby incorporated by reference, the conductivity of transition metal oxides (e.g., $CrO_3$, $Nb_2O_5$, $TiO_2$) is governed by electrical conduction at 298K. Therefore, the data relating to the breakdown of the $TiO_2$ layer will be interpreted according to Ikonopisov's model for avalanche breakdown, see Albella, J. M., I. Montero, and J. M. Martinez-Duart, A theory of avalanche breakdown during anodic oxidation, Electrochimica Acta, 1987, 32 (2): pp. 255–258; and Albella, J. M., et al., Dielectric breakdown processes in anodic $Ta_2O_5$ and related oxides: A Review, Journal of Materials Science, 1991, 26 (1991): pp. 3422–3432, the entire contents and disclosures of which are hereby incorporated by reference. According to this model and specifically for the case of $TiO_2$, the primary electronic current is injected from the electrolyte into the oxide valence hand as shown in FIG. 18. The high field strength existing within the oxide may accelerate these injected electrons to an energy that is sufficient to free secondary electrons by impact ionization. Hence, an avalanche may occur when a critical threshold current is reached causing electrical and subsequent mechanical breakdown. This typical avalanche behavior is displayed by both "Multilayer Sample 1" and "Multilayer Sample 2" in FIG. 12. One observation common to the avalanche mechanism is the reproducibility of breakdown voltages between samples within similar experimental conditions while the threshold current is known to vary. FIG. 13 illustrates the details of the $TiO_2$ breakdown behavior highlighting the characteristic voltage-current oscillations. Post-anodization removal of the alumina via chemical etch, and imaging with FESEM, clearly shows that the Ti oxide layer was preferentially removed from the corresponding alumina pore centers. The preferential etching of the $TiO_2$ at the pore centers is controlled by the alumina template. The applied voltage across both the $TiO_2$ and alumina pore wall is distributed such that dV/dx is small because dx is large (z 750 nm). This is not the case at the pore centers, which have incrementally removed the alumina barrier layer. The dV/dx is large because while dV remains constant, dx is now much smaller ($\approx$15 nm).

Figure 14:
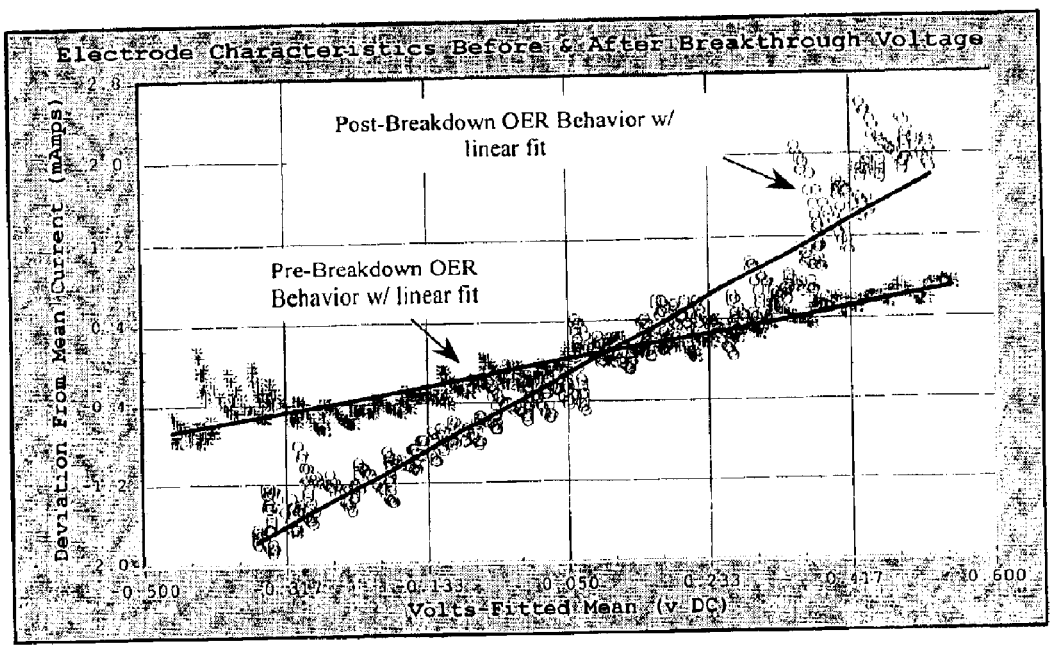
FIG. 14 shows a change in Tafel-like behavior of OER before and after $TiO_2$ breakdown, with raw current data and raw voltage data linearly fitted and respective means removed.

Analysis of the OER behavior before and after $TiO_2$ removal: Additional strong evidence for removal of the titanium oxide at the pore centers is the significant change in the Tafel-type slope immediately preceding and following the breakdown of the $TiO_2$ layer. FIG. 14 shows the change in the electrode behavior. The Tafel-type slope is observed to change by a factor of 3 within +/−1.5 volts of the breakdown voltage. The interpretation of this data requires considering the nature of the semiconducting properties of $TiO_2$ and the classical Butler-Volmer electrochemical kinetics, see Bard, A. J. and L. R. Faulkner, Electrochemical Methods: Fundamentals and Applications, Second ed. 2001, New York: John Wiley and Sons, 833, the entire contents and disclosure of which is hereby incorporated by reference. The OER occurring on the multilayer electrode displays Tafel-type behavior tip to 40 mAmps/cm$^2$ and mass-transfer limited behavior beyond this current. Using the Butler-Volmer model, the anodic slope of the redox reaction is $(1-\alpha)F/2.3RT$, where the transfer coefficient ($\alpha$) is a function of both the redox reaction occurring and the electrode surface involved. For metallic electrodes within the Tafel kinetically dominated region, it is observed that $0.3<\alpha<0.7$ due to the applied potential drop occurring primarily in the Helmholtz region of the double layer. As discussed in the present invention, bulk n-type $TiO_2$ ($E_g$=3.2 eV) produced by anodization, has electron bands pinned at the electrode/electrolyte interface by the existence of surface states and the strong interaction with water. As shown by Memming for bulk semiconductors, band pinning produces a space charge and subsequent depletion layer within the semiconductor when the Fermi level of the redox reaction ($E_{fredox}$) falls within the band gap of the semiconductor ($E_{gsemi}$), see Memming, R., Semiconductor Electrochemistry, 1998, Wiley-VCH: Weinheim, p. 394, the entire contents and disclosure of which is hereby incorporated by reference. As a result of this space charge behavior, semiconductor electrodes have typical values of $\alpha$ close to 1. As described in the present invention, it is recognized that the 20 nm nominal $TiO_2$ layer may be too thin to support a space charge layer and thus be dominated by interface kinetics as described by Lindquist, S. E., et al., Charge transport in nanostructured thin-film electrodes, in Electrochemistry of Nanomaterials, G. Hodes, Editor, 2001, Wiley-VCH: Weinheim, p. 310, the entire contents and disclosure of which is hereby incorporated by reference. Despite the origin of the $TiO_2$ electrode characteristics, a change in the slope of the Tafel-type behavior within +/−1.5 volts of the observed breakdown peak strongly suggests a change in electrode characteristics. There are two potential causes of this observed change in the transfer coefficient. The first possibility is the electrical/mechanical breakdown of the $TiO_2$ layer directly exposing the Pt underlayer to the electrolyte at the pore bases. The second possibility as described by Horrocks, B. R., M. V. Mirkin, and A. J. Bard, Scanning Electrochemical Microscopy: 25, Application to investigation of the kinetics of heterogeneous electron transfer at semiconductor (WeSe2 and Si) electrodes, Journal of Physical Chemistry, 1994, 98 (37): pp. 9106–9114, the entire contents and disclosure of which is hereby incorporated by reference, is the onset of electronic carrier degeneracy as the $E_{fsemi}$ is approached by either the pinned conduction band surface states or valence band surface states ($E_{esurf}$ or $E_{vsurf}$) in order to eliminate one of these two possibilities, an OER-UV light study was conducted and is discussed below.

Electrochemical analysis of alumina barrier layer removal: Direct FESEM examination of the barrier layer was difficult due to the lack of contrast and charging behavior of alumina and the $TiO_2$ sub-layer. Thus, an electrochemical means of verifying the presence or absence of the alumina barrier layer to help interpret the FESEM images may be utilized. Cyclic voltammetry was identified as the most straightforward electro-analytical technique due to the electrical conduction properties of the alumina barrier layer and the relative ease of peak interpretation.

Serebrennikova et al. employed a cyclic voltammetry technique in studying the electrochemical deposition of metals into nanoporous alumina, see Serebrennikova, I., P. Vanysek, and V. I. Birss, Characterization of porous aluminum oxide films by metal electrodeposition, Electrochemical Acta, 1997, 42 (1): pp. 145–151, the entire contents and disclosure of which is hereby incorporated by reference. The redox couple employed was $Ag/Ag^{2+}$ in dilute $H_2SO_4$ or borate buffer solution. Serebrennikova et al. showed that both anodically generated planar and porous alumina produced a rectification in the CV scans of the silver redox couple. To confirm the utility of this electrochemical approach, the CV behavior of three reference samples were examined as part of the present invention. The first reference sample was a thin film Pt on Si substrate for determination of peak location of the silver redox couple. The second reference sample was nanoporous alumina formed on bulk Al foil. As stated in the experimental CV discussion above, the bulk alumina template was anodized to the equivalent pore depth and diameter of the thin film based samples. The purpose of this anodized bulk Al reference sample was to establish the behavior of the alumina barrier layer and demonstrate the absence of the anodic silver stripping peak due to rectification produced by the barrier layer as observed in Serebrennikova, I., P. Vanysek, and V. I. Birss, Characterization of porous aluminum oxide films by metal electrodeposition, Electrochemical Acta, 1997, 42 (1): pp. 145–151, the entire contents and disclosure of which is hereby incorporated by reference. The third reference sample was an anodically converted 15 nm $TiO_2$ from e-beam deposited 8 run Ti with Pt underlayer on Si substrate. The Pt/Si and the anodized Ti/Pt/Si reference samples demonstrated an anodic stripping peak as well as a cathodic deposition peak with the $TiO_2$ creating approximately a +/−100 mV shift in peak location vs. the Pt thin film electrode. Hence, the absence of the silver anodic stripping peak was found to be unique to the presence of an alumina barrier layer at the pore bases. It is important to emphasize that the silver CV approach does riot discern between the absence and presence of a $TiO_2$ layer at the pore bases as currently applied due to the noisy behavior of the nanoporous electrodes.

Figure 15:
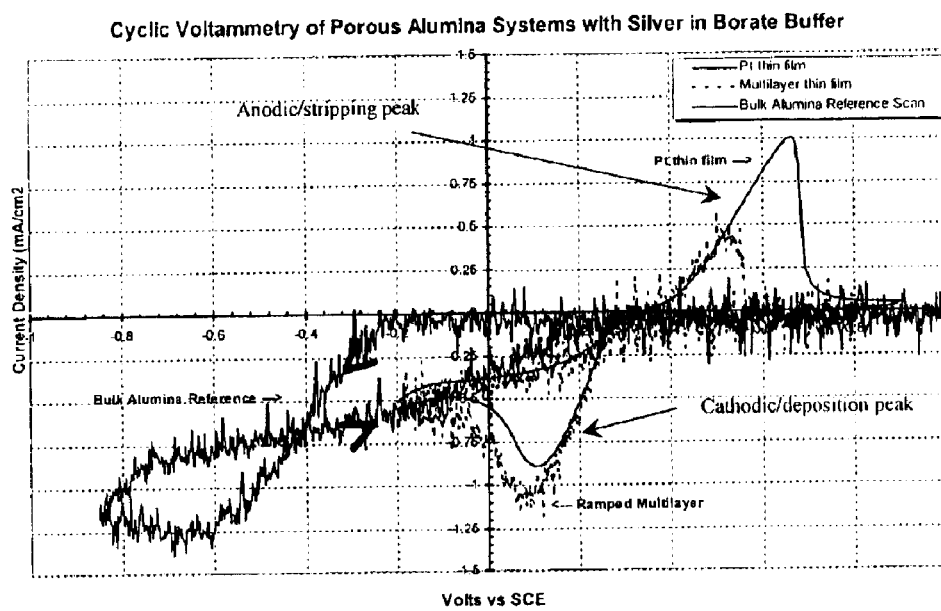
FIG. 15 shows cyclic voltammetry behavior of CV samples 1, 4 and 5 in which a Pt thin film electrode and bulk alumina electrode set the boundary conditions for the other samples.
Figure 16:
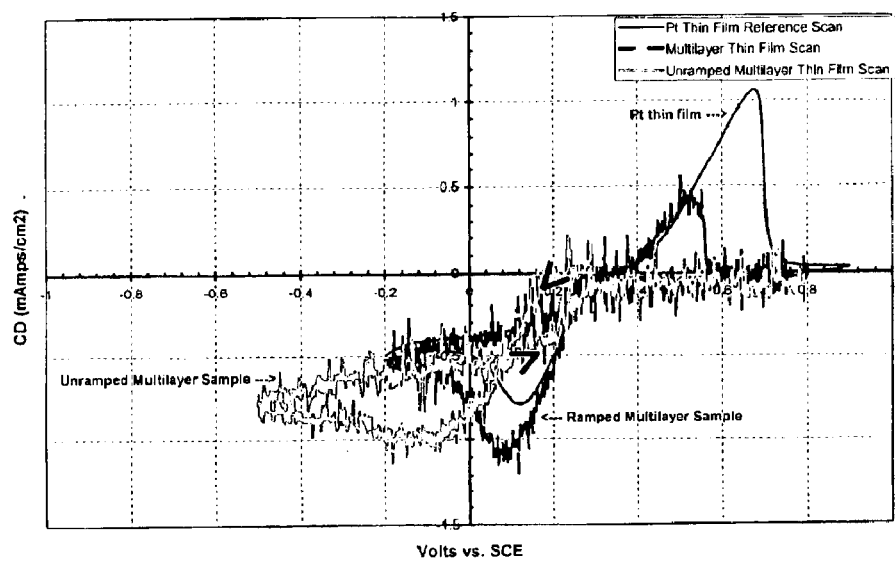
FIG. 16 shows cyclic voltammetry behavior of CV samples 1, 3 and 4 showing significant deviation of unramped behavior vs. a Pt thin film.
Figure 17:
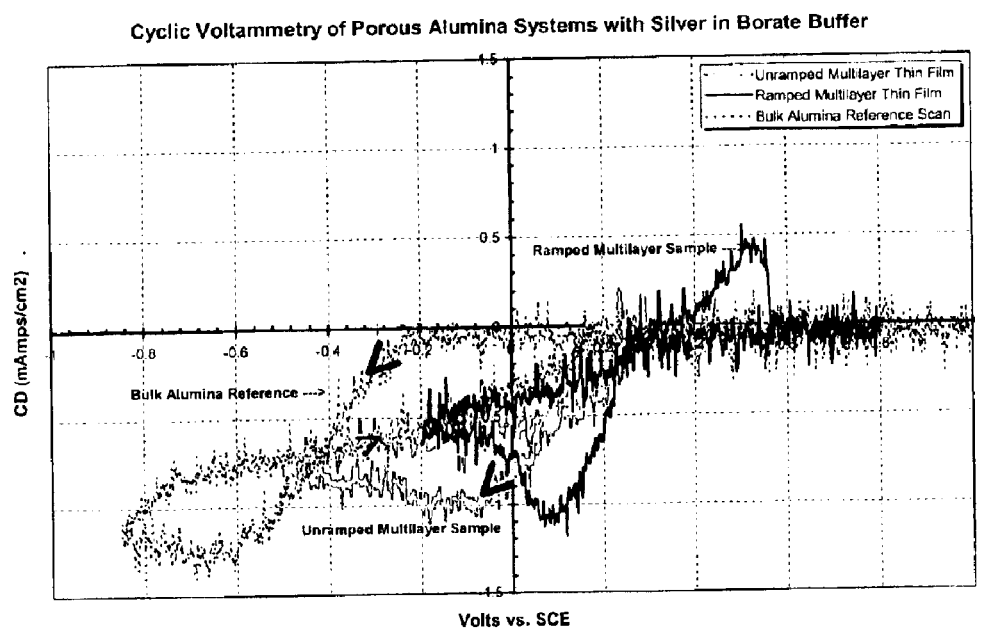
FIG. 17 shows cyclic voltammetry behavior of CV samples 3, 4 and 5 showing that the unramped sample matches the behavior of the bulk alumina reference.

Five types of samples as described in the cyclic voltammetry experimental section above and displayed in three figures (FIGS. 15, 16 and 17) are summarized here to understand the impact of voltage ramping on the alumina barrier layer. FIGS. 15, 16 and 17 show 30 nm Pt on Si substrate (CV Sample 1); anodically generated 15 nm $TiO_2$/30 nm Pt on Si (CV Sample 2); an unramped multilayer sample (CV Sample 3); a ramped to completion multilayer sample (CV Sample 4); and bulk alumina with pore depth held constant (CV Sample 5). FIGS. 15, 16 and 17 summarize the CV findings.

FIG. 15 compares the silver redox CV behavior of the Pt thin film reference (CV Sample 1), the bulk alumina reference sample (CV Sample 5), and the ramped multilayer (CV Sample 4). The Pt thin film on a Si substrate reference clearly shows the locations of both the anodic stripping peak at 0.67 volts vs. SCE and the cathodic deposition peak at 0.096 volts vs. SCE. The bulk alumina reference displays a hysteresis and a broad silver deposition peak around −0.65 volts vs. SCE. This hysteresis is most likely due to the polarization effect observed by Hickmott in bulk Al-anodized planar alumina-Au thin film MIM structures, see Hlickmott, T. W., Polarization measurements in anodized $Al-Al_2O_3$-Au diodes, Applied Physics Letters, 1999, 75 (19): pp. 2999–3001, the entire contents and disclosure of which is hereby incorporated by reference. Hence, the bulk alumina reference sample displays two distinct behaviors in the CV scans that are products of the existence of an alumina barrier layer at the pore bases. First, the absence of the anodic stripping peak is consistent with the known rectification behavior of alumina. Second, hysteresis in the cathodic deposition range is readily observed and is most likely due to polarization of the alumina barrier layer. Neither, the electronic conduction mechanism nor the source of the polarization current is known definitively for anodic alumina. It is widely believed that ion incorporation (e.g., $OH^-$, $HSO_4^{2-}$, $SO_4^{2-}$) during anodization plays a major role in both the conduction mechanism and the polarization current, Parkhutik, V. P. and V. Shershulsku, Theoretical modeling of porous oxide growth on aluminum, Journal of Applied Physics D, 1992, 25: pp. 1258, the entire contents and disclosure of which is hereby incorporated by reference. The ramped multilayer sample curve contains both a silver anodic stripping peak and a cathodic deposition peak, which match the Pt thin film electrode peak locations. The conclusion to be drawn from FIG. 15 is that the ramped multilayer sample (CV Sample 4) demonstrates CV behavior that more closely matches the Pt thin film reference sample than the bulk alumina reference sample.

FIG. 16 compares the silver redox CV behavior of the Pt thin film reference (CV Sample 1), unramped multilayer sample (CV Sample 3) and ramped multilayer sample (CV Sample 4). Three observations are clear from FIG. 16. First, the unramped multilayer sample does not display an anodic stripping peak compared to the observed anodic peaks in the other two samples. Second, for the unramped multilayer sample, there is a small but observable hysteresis region at the onset of cathodic voltages due to polarization effects. Third, the ramped multilayer sample scans in both FIGS. 15 and 16 demonstrate anodic and cathodic peaks that more closely match the Pt thin film reference behavior vs. the unramped multilayer sample and the bulk alumina reference.

FIG. 17 compares the CV behavior of the bulk alumina reference sample (CV Sample 5), unramped multilayer sample (CV Sample 3), and ramped multilayer sample (CV Sample 4). Three observations may readily be made from FIG. 17. First, the ramped multilayer sample displays unequal areas for the cathodic deposition peak and the anodic stripping peak. The most likely cause for this is incomplete barrier layer etching in limited areas of the sample. Second, a significant peak shift for the deposition of silver between bulk alumina and unramped multilayer samples is due to an observed thinning of the barrier layer in the thin film structure. Third, the much larger hysteresis effects demonstrated by the bulk alumina sample vs. the unramped multilayer thin film sample appear to be a function of alumina barrier layer thickness and thus consistent with Hickmott's polarization behavior.

Compiling the results from FIGS. 15, 16 and 17, it is clear that ramped and unramped multilayer samples behave very differently. Ramped multilayer samples display both an anodic stripping peak and a cathodic deposition peak with only minimal shift in peak location as compared to a thin film Pt reference sample or the $TiO_2$/Pt reference sample. The unramped multilayer sample CV results closely match the bulk alumina reference sample both in terms of the absence of the anodic stripping peak due to barrier layer rectification and the hysteresis/polarization effect observed in the cathodic portion of the scan. The cathodic peak shift and the magnitude of the hysteresis based polarization effects for the bulk alumina sample vs. the unramped multilayer sample are most likely due to the observed alumina barrier layer thinning in the thin film based sample vs. the bulk alumina reference sample. Based on the above CV information, it may be stated that the ramping of $\Delta V_{applied}$ in the anodization program is shown to remove the alumina barrier layer from an electrochemical CV standpoint.

Examination of the $TiO_2$ layer via OER-UV light mechanism: The presence of the $TiO_2$ layer as the active electrode material at the pore bases is examined by the present invention by illuminating the working electrode with UV light and recording the resulting impact of EHP generation in the semiconductor electrode ($TiO_2$). Two complimentary approaches are analyzed. The first is an equilibrium approach where the impact of UV light on the open circuit potential ($E_\infty$) is measured with reference to an Ag/AgCl reference electrode. The second is a kinetic approach, where the electrochemical cell is polarized to the onset of the OER in an aqueous based borate buffer solution and the UV light is cycled while the change in current is monitored.

The impact of UV light on the OER at a bulk single crystal $TiO_2$ semiconductor electrode was first studied by Fujishima, A. and K. Honda, Electrochemical photolysis of water at a semiconductor electrode, Nature, 1972, 238 (July 7): pp. 37–8, the entire contents and disclosure of which is hereby incorporated by reference. The reaction mechanism discussed in Fujishima's study of the $TiO_2$-Pt water photohydrolysis has been recently reexamined by Bak, T., et al., Photo-electrochemical properties of the $TiO_2$-Pt system in aqueous solutions, International Journal of Hydrogen Energy, 2002, 27 (2002): pp. 19–26, the entire contents and disclosure of which is hereby incorporated by reference. FIG. 18 displays the OER mechanism in the dark/short circuited state showing the equivalence of the Fermi Level ($E_{fsemi}$) in the semiconductor and the Fermi Level ($E_{fRedox}$) of the redox couple as described by the Gerischer Model of electrolytes, see Memming, R., Semiconductor Electrochemistry, 1998, Wiley-VCH: Weinheim, p. 394, the entire contents and disclosure of which is hereby incorporated by reference. For the open circuit behavior of an n-type $TiO_2$ semiconductor electrode, the anodic exchange current ($jo^{anod}$) is due to the availability of thermally generated holes, and the equivalent cathodic exchange current ($jo^{cath}$) is due to surface states, tunneling and various flaws allowing electron transfer to the conduction band. When the sample is first illuminated in the open circuit condition, there is a brief transient response of hole dominated flow to the interface while electron flow is limited by the conduction band bending and hence the resulting voltage barrier ($V_s$) at the interface. This builds a positive charge that lowers $V_s$ until electrons can reach the surface at the same rate as holes. The net effect of this lowering of $V_s$ is the $E_{fsemi}$ moves down on the energy axis relative to $E_{fRedox}$. However, at the Pt metal electrode, there is negligible change due to illumination if the localized heating effects of the solution are factored out. Thus, the voltage measured by the equilibrium $E_{OC}$ experiment is $E_{fsemi}-E_{0ref}$ (Ag/AgCl) as a function of UV light illumination and therefore EHP generation.

The kinetic approach allows the ratio of thermally generated minority carriers to light-induced generation of minority carriers to be measured via the change in OER reaction current upon illumination. According to the Schottky barrier model, the applied potential creates both a $\Delta\phi_H$ within the Helmholtz layer of the double layer and $\Delta\phi_{SC}$ within the space charge layer near the electrode interface, see Memming, R., Semiconductor Electrochemistry, 1998, Wiley-VCH: Weinheim, p. 394, the entire contents and disclosure of which is hereby incorporated by reference. While $\Delta\phi_{SC}$ is essentially constant for non-degenerate semiconductors, it is the $\Delta\phi_{SC}$ that drives the degree of band bending in the semiconductor electrode and hence the relative concentrations of charge carriers. For minority carrier reactions, the holes generated by light within the space charge region are driven toward the interface by the electric field and transferred across the interface. The rate of hole transfer across the interface is proportional to the photocurrent. Thus, this kinetic experiment examines the working electrode's sensitivity to UV-light via EHP generation and subsequent efficiency of charge carrier transfer to the electrolyte.

Lindquist et al., see Lindquist, S. E., B. Finnstrom, and L. Tegner, Photoelectrochemical properties of polycryslalline $TiO_2$ thin film electrodes on quartz substrate, Journal of the Electrochemical Society, 1983, 130 (2): pp. 351–358, the entire contents and disclosure of which is hereby incorporated by reference, examined the photoelectrochemical properties of polycrystalline $TiO_2$ thin film electrodes on quartz substrates and determined the validity of the space charge mechanism (Schottky barrier model) as a function of semiconductor electrode thickness. Although, the furnace oxidized $TiO_2$ was found to have high donor concentrations and space charge layer thickness to total oxide thickness ratios in the range of 0.11–0.14 (w/d), the Schottky Barrier model and thus the optical behavior as predicted by the Gartner-Butler expression, see Lindquist, S. E., et al., Charge transport in nanostructured thin-film electrodes, in Electrochemistry of Nanomaterials, G. Hodes, Editor, 2001, Wiley-VCH: Weinheim. p. 310, the entire contents and disclosure of which is hereby incorporated by reference, was found to breakdown as the thickness of the $TiO_2$ layer became smaller than 40 nin. Flat band behavior and interface kinetics were demonstrated to dominate the optical behavior of $TiO_2$ electrodes with a thickness less than 35 nm. The charge transport mechanisms operating in this regime are reviewed by Lindquist, S. E., et al., Charge transport in nanostructured thin-film electrodes, in Electrochemistry of Nanomaterials, G. Hodes, Editor, 2001, Wiley-VCH: Weinheim. p. 310, the entire contents and disclosure of which is hereby incorporated by reference, and described transport mainly in terms of charge diffusional gradients and carrier lifetimes. Therefore, the thin $TiO_2$ diffusion layer (d≈20 nm) present in the present invention most closely follows the mechanisms described by Lindquist. However, the bulk space charge model of semiconductors allows more intuitive insight into the OER-UV light interaction and its applicability in determining the characteristics of the working electrodes under study. The bulk space charge layer argument vs. the flat band mechanism does not change the net result of a specific OER-UV light interaction for $TiO_2$ electrodes.

Four samples were used in both the $E_{OC}$ and the kinetic OER-UV light analysis: (1) Sample ID: Ramp 1—no voltage ramping-potentiostatic anodization; (2) Ramp 2—voltage ramped pre-breakdown of $TiO_2$ layer; (3) Ramp 3—voltage ramped post-breakdown of $TiO_2$ layer; and (4) Pt Electrode—thin film Pt on Si substrate.

Figure 19:
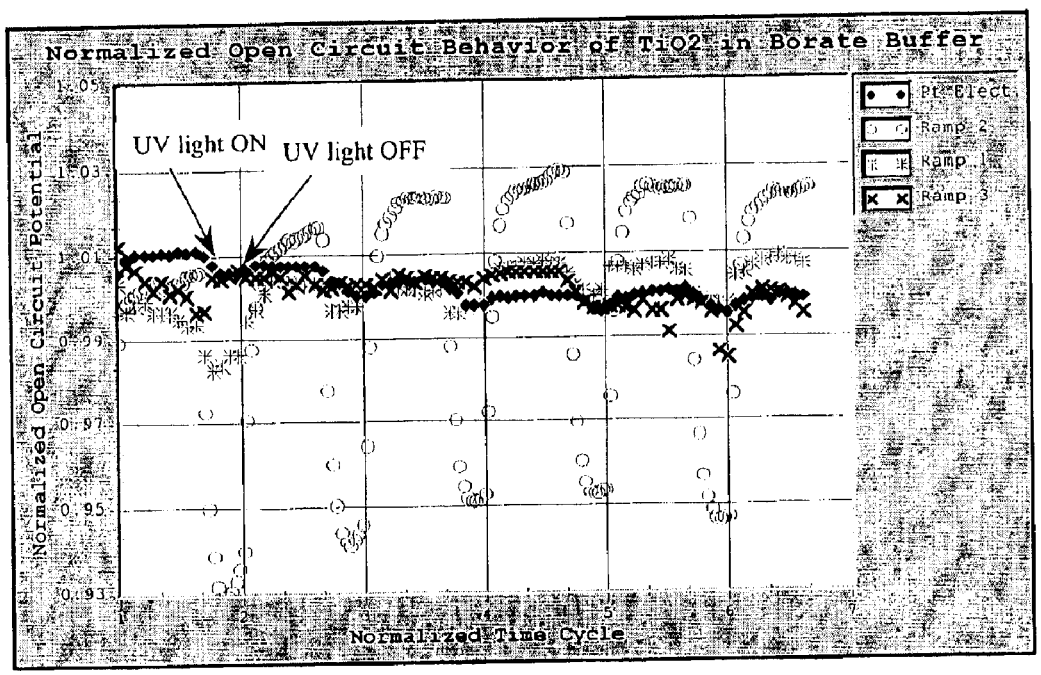
FIG. 19 shows normalized EOC behavior of multilayer template samples upon ultraviolet (UV) illumination, with samples compared at various voltage ramping points (1, 2 and 3) during post-anodization.

FIG. 19 displays the results of the EDC study in borate buffer. The raw $E_{OC}$, data has been normalized by scaling the data with the mean $E_{OC}$ value for each respective sample.

Figure 20:
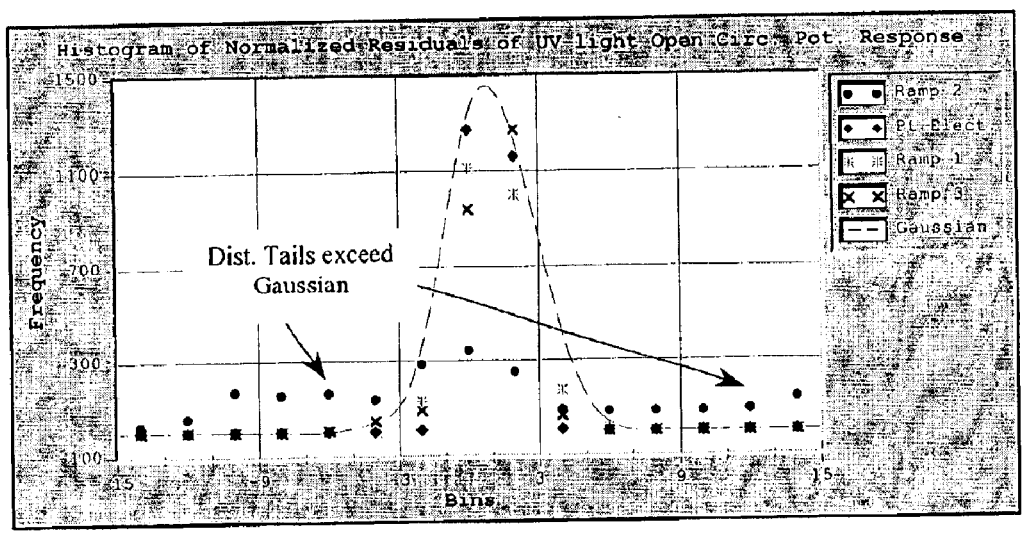
FIG. 20 shows a histogram of stochastic residuals from EOC data using the Moussa and Cheema method where Gaussian distribution bounds the stochastic data from statistically significant data.

The raw timescale in seconds has been scaled by the total period of 90 seconds. Therefore, the normalized $E_{OC}$ data expresses the relative impact of the UV light on each sample. Only the magnitudes of relative voltage changes are an important parameter: the sign of the voltage change upon illumination is irrelevant. It may be observed from FIG. 19, that the most significant UV light sensitivity is sample Ramp 2. Samples Ramp 1 and 3 are observed to have relative changes of $E_{OC}$ upon illumination similar to that of the Pt electrode sample. The normalized $E_{OC}$ data of the various samples was then fitted nonparametrically to an optimized cubic smoothing spline curve as described by Moussa, M. A. A. and M. Y. Cheema, Non-parametric regression in curve fitting, The Statistician, 1992, 41 (1992): pp. 209–225, the entire contents and disclosure of which is hereby incorporated by reference, with a smoothing parameter k that minimized the generalized cross-validation criterion. This statistically optimized trend was then removed from the data to provide the stochastic portion of the $E_{OC}$ data. Application of the Central Limit Theorem to the stochastic residuals as stated by Box, G. E. P., W. G. Hunter, and J. S. Hunter, Statistics for Experimenters: An introduction to design, data analysis, and model building, 1 ed., Wiley Series in Probability and Mathematical Statistics, ed. R. A. Bradley, Vol. 1, 1978, New York: John Wiley and Sons, the entire contents and disclosure of which is hereby incorporated by reference, predicts that a Gaussian distribution will bound the stochastically generated data plotted in a histogram Format. Deviations from the Gaussian bounding behavior demonstrate a statistically relevant source such as strong $TiO_2$-UV light interaction beyond typical thermal solution effects. This is demonstrated in FIG. 20 where sample Ramp 2 contains distribution tales that exceed the bounding Gaussian. Samples Ramp 1, Ramp 3 and the Pt electrode are contained within the bounding Gaussian and therefore have no statistically significant interaction with UV light beyond thermal solution effects.

Figure 21:
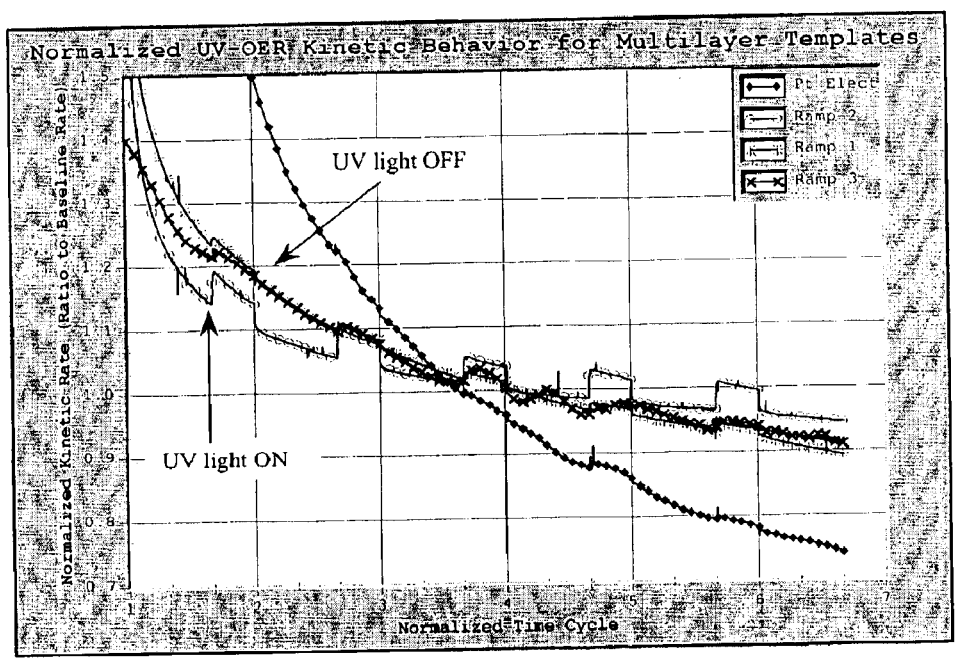
FIG. 21 shows normalized OER kinetic behavior of multilayer template samples upon UV illumination, with the same ramping schedule, potentiostatically polarized in borate buffer electrolyte.
Figure 22:
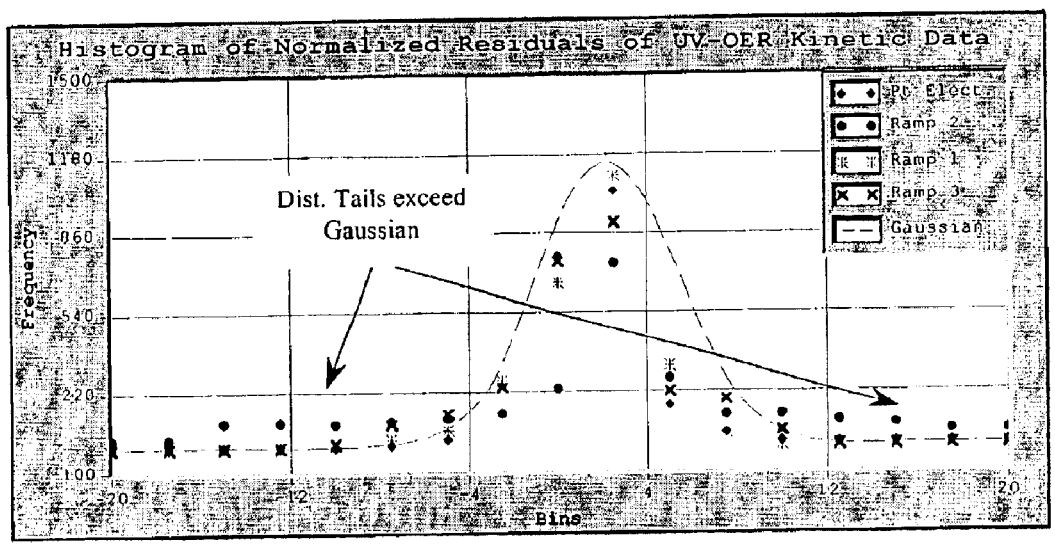
FIG. 22 shows a histogram of stochastic residuals from OER kinetic data using the Moussa and Cheema method where Gaussian distribution bounds the stochastic data from statistically significant data.
Figure 23:
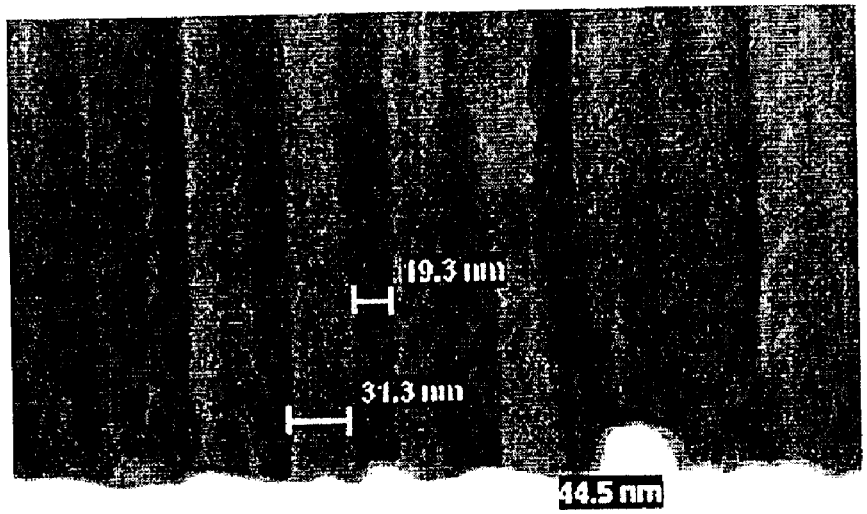
FIG. 23 shows a FESEM micrograph (150 kX) of sample (Ramp 2) post-UV examination, where the image suggests removal of a typical alumina barrier layer and presence of a $TiO_2$ layer at pore bases, and where the $TiO_2$ layer is a working electrode material that interacts with UV light.

The kinetic behavior is shown in FIG. 21 normalized by the equivalent procedure as described above for the $E_{OC}$, data. Again, it may be observed that sample Ramp 2 displays the highest degree of relative enhancement of the OER rate upon illumination. Samples Ramp 1 and 3 show relative changes of reaction rate with UV illumination comparable to the Pt electrode sample. FIG. 22 shows the detrended stochastic residuals as calculated by the Moussa and Cheema method described above. The application of the central limit theorem and fitting a bounding Gaussian distribution allows the determination of statistically significant OER-UV light interaction beyond thermal solution effects. The sample Ramp 2 is not bounded by the Gaussian distribution toward the tails. Samples Ramp 1, Ramp 3 and the Pt electrode are contained within the bounding Gaussian and therefore have no statistically significant interaction with UV light beyond thermal solution effects.

Summarizing the OER-UV light results, it is clear that the multilayer samples respond differently to UV light as a function of the applied voltage within the voltage ramping program. The OER-UV light results suggest that the multilayer template is statistically most sensitive to UV light in the region just prior to the observed current oscillations (sample Ramp 2) shown in FIG. 13 indicating the breakdown of the thin $TiO_2$ layer. The subsequent reduction in UV light sensitivity shown by sample Ramp 3, post-breakdown, suggests that the working electrode material at the base of the pores is no longer $TiO_2$. Thus, the OER-UV light study in conjunction with the observed current oscillations during the voltage ramping program discussed in the present invention and the change in Tafel-type slope of the OER discussed in the present invention are all consistent with removal of $TiO_2$ through an avalanche breakdown mechanism with exposure of the Pt underlayer as a working electrode material.

The present invention provides an understanding as to how a nanoporous alumina template may be engineered to have the desired characteristics for subsequent electrochemical deposition of nanowires. This is achieved through the use of a multilayer thin film based precursor on an arbitrary substrate. In order to most efficiently achieve the goal of creating a Pt electrode at the pore bases, the electrically insulating alumina barrier layer intrinsically created by the anodization process may be removed in situ. Previous experimental work, see O'Sullivan, J. P. and G. C. Wood, The morphology and mechanism of formation of porous anodic films on aluminum, Proceedings of the Royal Society of London, A., 1970, 317 (1970): pp. 511–543; Vorobyova, A. I. and E. A. Outkina, Study of pillar microstructure formation with anodic oxides, Thin Solid Films, 1998, 1–2 (Jul. 1, 1998): p. 324; and Tatarenko, N. J., V. A. Solntseva, and A. N. Rodionov, Novel nanoscale field emission structures: Fabrication technology, experimental and calculated characteristics, Journal of Vacuum Science and Technology B, 1999, 17 (2): pp. 647–6546, the entire contents and disclosure of which are hereby incorporated by reference, examined the dynamics of the alumina barrier layer and established that through the applied voltage, the electric field present in the alumina barrier layer governed the resulting anodic alumina characteristics. This was cast in more formal mathematical terms by Thamida, S. K. and H. C. Chang, Nanoscale pore formation dynamics during aluminum anodization, Chaos, 2002, 12 (1): pp. 240–251, the entire contents and disclosure of which is hereby incorporated by reference, which advanced a fundamental understanding of the parameters governing the metal/oxide interface and oxide/electrolyte interface propagation. Pore depth is readily controllable through the thickness of the available thin film Al precursor deposited on the substrate and pore diameter by the applied voltage. However, in order to achieve an in sites generated Pt electrode at the pore bases, the electric field across the alumina barrier layer after the endpoint of alumina anodization must be controllable. Therefore, the problems of Al—Pt intermetallic formation and Pt-catalyzed OER was recognized and solved in the present invention. The multilayer template described herein using a thin film Ti diffusion barrier has been demonstrated to achieve the goals of the present invention. E-beam deposited Ti was shown to have the following four characteristics: (1) the ability to deposit the barrier material of choice in the same physical vapor deposition device as Al and Pt layers; (2) limited intermetallic formation with Al and Pt layers at ambient substrate temperatures with good mechanical adhesion characteristics; (3) an anodization product of the barrier layer material that is stable and may selectively be removed at the pore centers by an in situ technique; and (4) an anodization product of the barrier layer preferably supresses the OER to allow the field driven barrier layer removal of alumina at pore bases.

Multiple analytical techniques were used to examine and verify the anodization behavior of the multilayer template. The CV study of the silver redox couple, in a similar manner to Serebrennikova, I., P. Vanysek, and V. I. Birss, Characterization of porous aluminum oxide films by metal electrodeposition, Electrochemical Acta, 1997, 42 (1): pp. 145–151, the entire contents and disclosure of which is hereby incorporated by reference, demonstrated electrochemically that the voltage ramping program allowed for incrementally removing: the alumina barrier layer but did not determine the absence or presence of $TiO_2$ at the pore bases. The removal of $TiO_2$ at the pore bases was established by: (1) avalanche breakdown current oscillations observed during the voltage ramping program; (2) the sharp change in Tafel-type slope of the OER before and after the $TiO_2$ breakdown; (3) the UV-OER response observed both from equilibrium EOC and kinetic polarized OER approaches demonstrating pre-breakdown samples to be the only samples from the data set showing statistically significant UV-OER interaction; (4) the UV-OER data reduction analysis and statistical deviation from the bounding Gaussian behavior for pre-breakdown samples showing statistically significant UV light interaction that exceeds thermal solution effects; and (5) the FESEM examination of the anodized multilayer samples terminated at various points within the anodization program demonstrates the evolution and removal of the alumina barrier layer and $TiO_2$ layer.

The thin film based multilayer template described by the present invention has been shown to achieve the goal of an optimum nanostructured template for subsequent electrochemical deposition of nanowire materials. The present invention may be extending into various related areas by one of ordinary skill in the art, such as substituting an optically transparent, electrically conductive material (i.e. ITO) for the Pt underlayer or integration of silicon-based circuitry with the nanostructured material.

Application to biosensors: A preferred embodiment of the present invention provides for a biosensor for the rapid detection of biomolecules. Such a biosensor may be used to detect antibodies, bacteria and proteins in a variety of environments, e.g. clinical diagnostics, food analysis and environmental monitoring. Nanostructured materials which are fabricated using the thin film multilayer template of the present invention may be used as the substrate to immobilize a biorecognition layer. Electrochemical detections may be applied as the direct, label-free, and fast measurements of the analytes.

Initial efforts to develop a biosensor were focused on the detection of bacteria, such as *E. coli* bacteria. *E. coli* is a type of bacteria commonly found in the intestines of healthy humans and animals. However, *E. coli* O157:H7 is an emerging cause of foodborne and waterborne illness because it can produce a powerful toxin. *E. coli* can easily contaminate ground beef, raw milk and chicken, therefore rapid and reliable identification and control of this pathogen is extremely important, see Buchanan, R. L., Doly, M. P., Foodborne disease significance of *E. coli* 0157:H7 and other enterohemorrhagic *E. coli*, Food Technol., 1997, 51 (10), pp. 69–76; Ivnitski, D., Abdel-Hamid, I., Atanasov, P., Wilkins, E., Biosensors for detection: of pathogenic bacteria, Biosensors & Bioelectronics, 1999, 14, pp. 599–624; Griffin, P. M., Tauxe, R. V., The epidemiology of infections caused by *E. coli* Ol 57:H7 and other Enterohemorrhagic *E. coli*, and the associated hemolytic-uremic syndrome, Epidemiol. Rev., 1991, 13, pp. 60–98; Miyai, K. A. P., C. P., Problems for improving performance in immunoassay, JIFCC, 1992, 4, pp. 154–163, the entire contents and disclosures of which are hereby incorporated by reference. Under the Safe Drinking Water Act, the EPA requires public water systems to monitor for coliform bacteria, including *E. coli*. The effective testing of bacteria requires the analysis methods meet a number of challenging criteria. Time and sensitivity of analysis are the most important limitations. Although standard microbiological techniques allow the detection of a single bacterium, amplification of the signal is required through growth of a single cell into a colony. This process is relatively time-consuming and costly. Considerable effort is now directed towards the development of methods that can rapidly detect low concentrations of bacteria in water, food and clinical samples.

Electrochemical detection techniques are promising alternatives to some existing detection, methods, such as optical assays, see Ivnitski, D., Abdel-Hamid, I., Atanasov, P., Wilkins, E., Biosensors for detection of pathogenic bacteria, Biosensors & Bioelectronics, 1999, 14, pp. 599–624; Ghindilis, A. L., Atanasov, P., Wilkins, M., Wilkins, E., Immunosensors: electrochemical sensing and other engineering approaches, Biosensors & Bloelectronics, 1998, 13 (1), pp. 113–131; and Warsinke, A., Benkert, A., Scheller, F. W., Electrochemical immunoassays, Fresenius J. Anal. Chem., 2000, 366, pp. 622–634, the entire contents and disclosures of which are hereby incorporated by reference. Electrochemical devices offer high sensitivity and are more amenable to miniaturization and integration, see Ivnitski, D., Abdel-Hamid, I., Atanasov, P., Wilkins, E., Biosensors for detection of pathogenic bacteria, Biosensors & Bioelectronics, 1999, 14, pp. 599–624; Ghindilis, A. L., Atanasov, P., Wilkins, M., Wilkins, E., Immunosensors: electrochemical sensing and other engineering approaches, Biosensors & Bloelectronics, 1998, 13 (1), pp. 113–131; Warsinke, A., Benkert, A., Scheller, F. W., Electrochemical immunoassays, Fresenius J. Anal. Chem., 2000, 366, pp. 622–634; and Sethi, R. S., Transducer aspects of biosensors, Biosensors & Bioelectronics, 1994, 9, pp. 243–264, the entire contents and disclosures of which are hereby incorporated by reference. In addition, the continuous response of an electrode system allows for on-line control and the equipment required for electrochemical analysis is simple and cheap compared to most other analytical techniques. Therefore, in the present invention, electrochemical transducers, such as electrochemical impedance and cyclic voltammetry may be applied to detect a specific enzymatic reaction or the formation of an antigen and antibody complex.

The nanostructured materials described herein may be used as the solid support to immobilize biomolecules. The ability to tailor a material's properties at the nanoscale level enables the development of a whole generation of devices that take advantage of the size scale by achieving high performance. With integration and miniaturization, biosensor technologies such as microspot assays and nanochip technologies further reduce costs and enhance throughput, see Griffiths, D., Hall, G., Biosensors-What real progress is being made?, Trends Biotechnol., 1993, 11, pp. 122–130; Goepel, W., Chemical sensing, molecular electronics, and nanotechnology: interface technologies down to the molecular scale, Sensors Actuators B, 1991, 4, pp. 7–21; Cheng, I. F., Whiteley, L. D., Martin, C. R. Q, Ultraunicroelectrode Ensembles. Comparison of Experimental and Theoretical Responses and Evaluation of Electroanalytical Detection Limits, Anal. Chem., 1989, 61, pp. 762–766; Owen, V. M., Market requirements for advanced biosensors in healthcare, Biosensors & Bioelectronics, 1994, 9, pp. XXIX–XXXV; and Roco, M. C., Williams, R. S., Alivisatos, P., Nanotechnology Research Directions: Vision for Nanotechnology in the Next Decade, IWGN Workshop Report, 1999, Dordrecht, The Netherlands, Kluwer Academic Publishers, the entire contents and disclosures of which are hereby incorporated by reference.

Figure 24A:
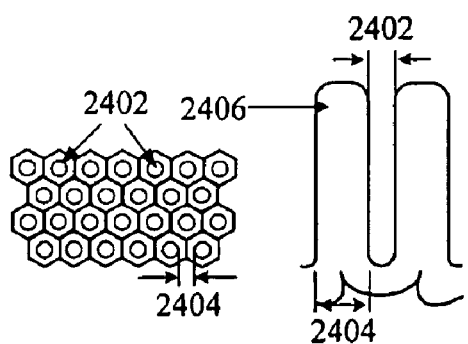
FIGS. 24A and 24B show a nanoporous aluminum oxide film formed by anodization.
Figure 24B:
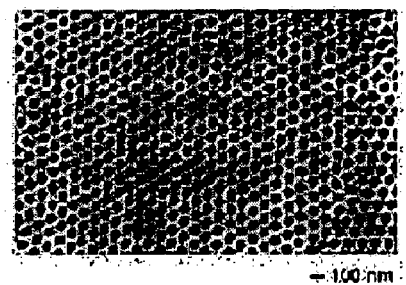

The nanostructured solid support used to immobilize the biological sensing elements for the biosensor application may be made by the template synthesis methods described in the present invention. Initially, the porous aluminum oxide film serves as the template. When aluminum is anodized in an appropriate acidic electrolyte under controlled conditions, it oxidizes to form a hydrated aluminum oxide (alumina) containing a two dimensional organized hexagonal array of cylindrical pores (FIGS. 24A and 24B), see also O'Sullivan, I. P., Wood, G. C., The Morphology and Mechanism of Formation of Porous Anodic Films on Aluminum, Proceedings of the Royal Society of London, Series A, Mathematical and Physical Science, 1970, 317 (1531), pp. 511–543, the entire contents and disclosure of which is hereby incorporated by reference. FIG. 24A shows pores 2402 and cell walls 2404 dispersed in alumina 2406. The pore diameter and the interpore spacing depend primarily on the applied electrical potential and in a secondary fashion on electrolyte pH, temperature and aluminum microstructure (grain size). The anodization parameters may be precisely controlled to form pore diameters from approximately 5 to approximately 100 inn and pore depths may be several microns, but typically less than 100 microns.

The nanoporous alumina template has been first used as a synthetic host for the electrochemically deposited materials, such as gold or silver or conductive polymers. Gold has been chosen as a preferable substrate material for the application to the *E. coli* immunosensor. Gold may be deposited into the pores of the template by AC electrochemical seeding of the pore bottom in an electrolyte, such as 1 g/L $HAuCl_4.3H_2O$ with 7 g/L $H_2SO_4$, and then followed by electroless growth of gold wires inside the pores using a commercial electroless plating solution, such as Neorum TWB solution (Uyemura International Corporation).

Figure 25:
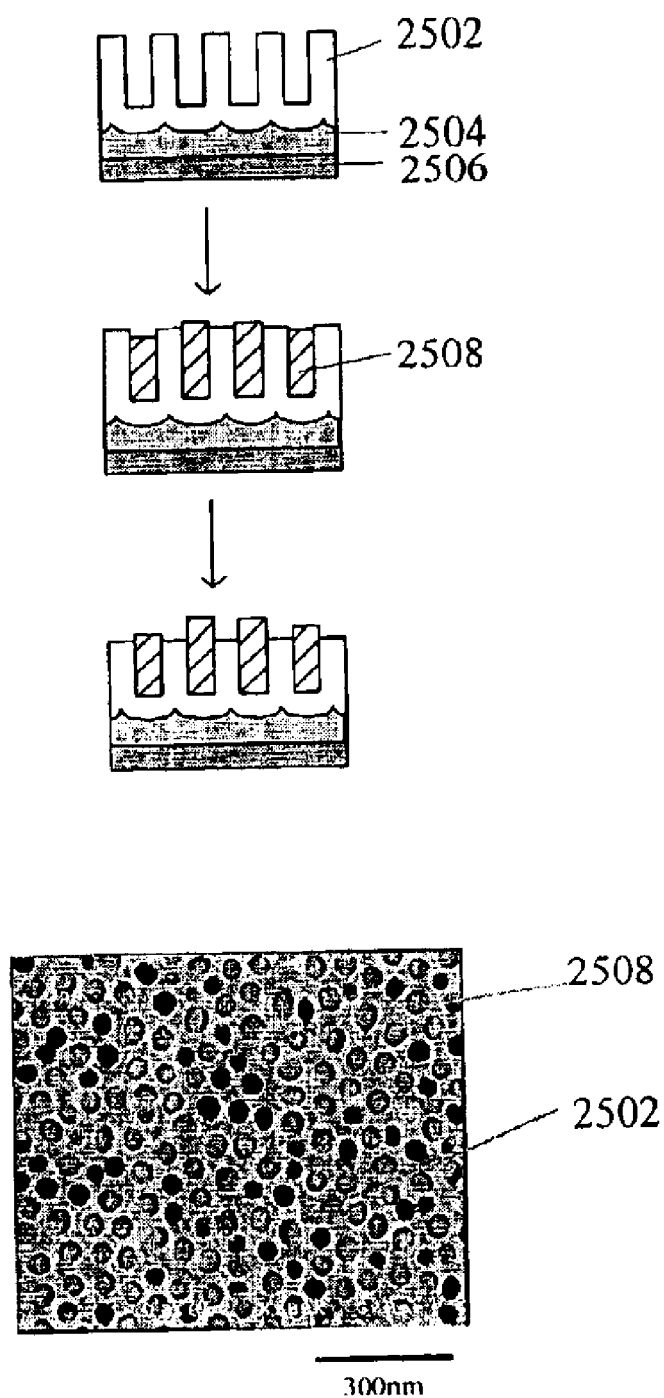
FIG. 25 shows an alumina template filled with metal.
Figure 26:
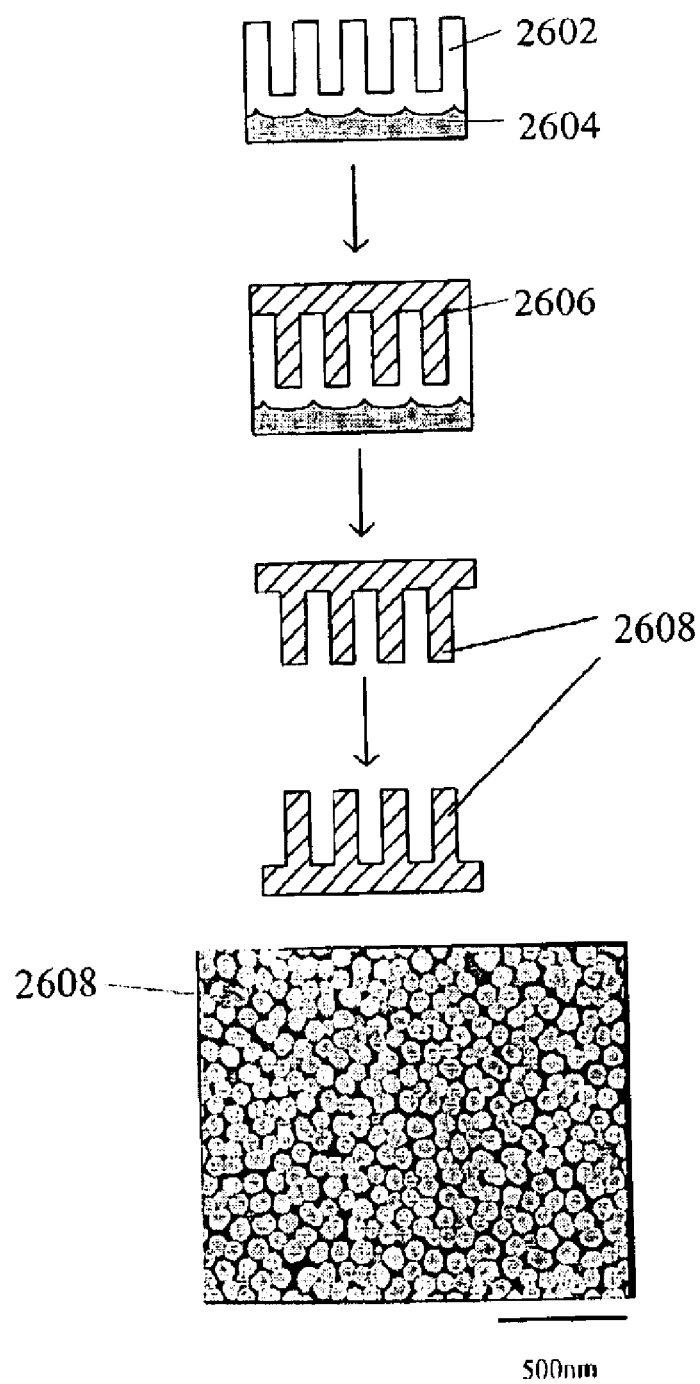
FIG. 26 shows an alumina template filled with a metal to form nano wires.

Depending on the intended application, the aluminum oxide matrix may either be left in-place or removed to produce a nanopatterned metal surface as shown in FIGS. 25 and 26. FIG. 25 shows a well-ordered porous layer of $Al_2O_3$ 2502 formed by anodization of aluminum metal. Aluminum 2504 beneath the oxide layer is the aluminum that has not been consumed by the anodization process. The template is supported by a conductive support 2506. Metal 2508, such as gold or silver or conductive polymers, may be deposited in the ordered pores of $Al_2O_3$ 2502 to form a nanostructured substrate for the immobilization of biorecognition elements. The length of the metal posts inside the pores may be controlled by controlling the time of electroless deposition. In FIG. 26, metal 2606 is overplated on top of the oxide layer 2602 during the electroless plating process. Then, both the oxide 2602 and aluminum metal 2604 which has not been anodized are dissolved in an acid, such as 1M $H_3PO_4$, or an alkaline solution, such as 1.5M NaOH. Flipping over the thin metal sheet 2606 yields a layer of metal with metal nanowires protruding from the surface like bristles of a brush.

The thin film multilayer of the present invention has greatly simplified the manufacturing process of the nanostructured materials. Because of the elimination of the barrier layer of nanoporous alumina oxide and the conductive surface at the pore base, direct current (DC) deposition may be used to fabricate nano metal posts or dots. The thickness of the template and also the dimension of the nano material inside the template may be precisely controlled. The templated nanoscale materials growing on the conductive surface are easier to integrate with integrated circuit (IC) circuitry.

Figure 30A:
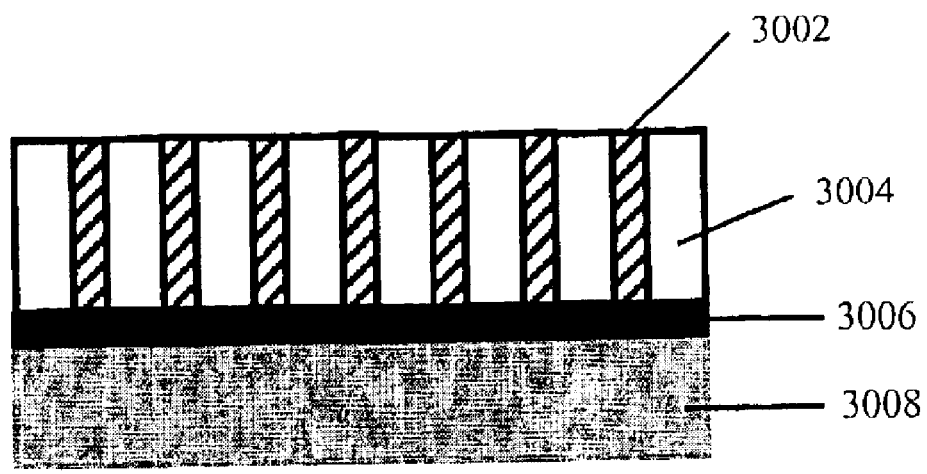
FIGS. 30A and 30B show cross-section views of the formation of nanostructured material devices based on a multilayer template of the present invention.
Figure 30B:
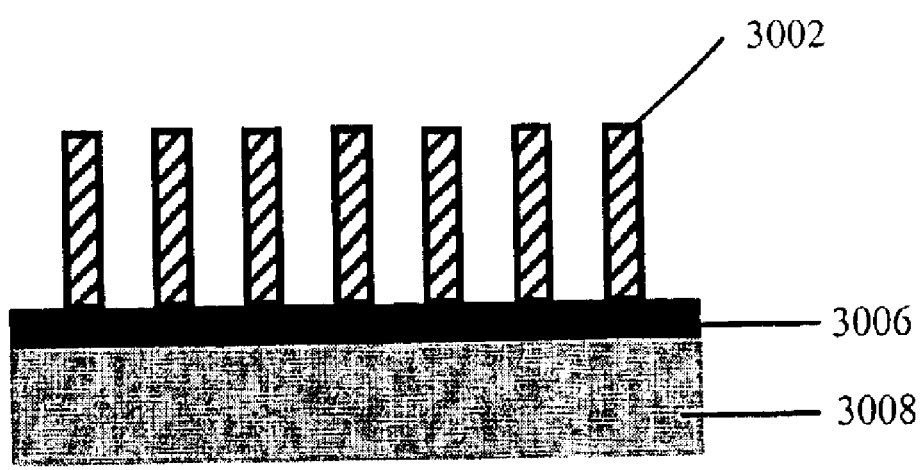

FIGS. 30A and 30B show nanostructured materials fabricated using the multilayer template of the present invention. The metal or polymer wires or dots 3002 are embedded in the aluminum oxide layer 3004 and directly sit on the conductive surface 3006, such as platinum, at the oxide pore base. An arbitrary substrate 3008 may be present as the mechanical support. The oxide layer 3004 may be dissolved according to different applications.

Figure 31:
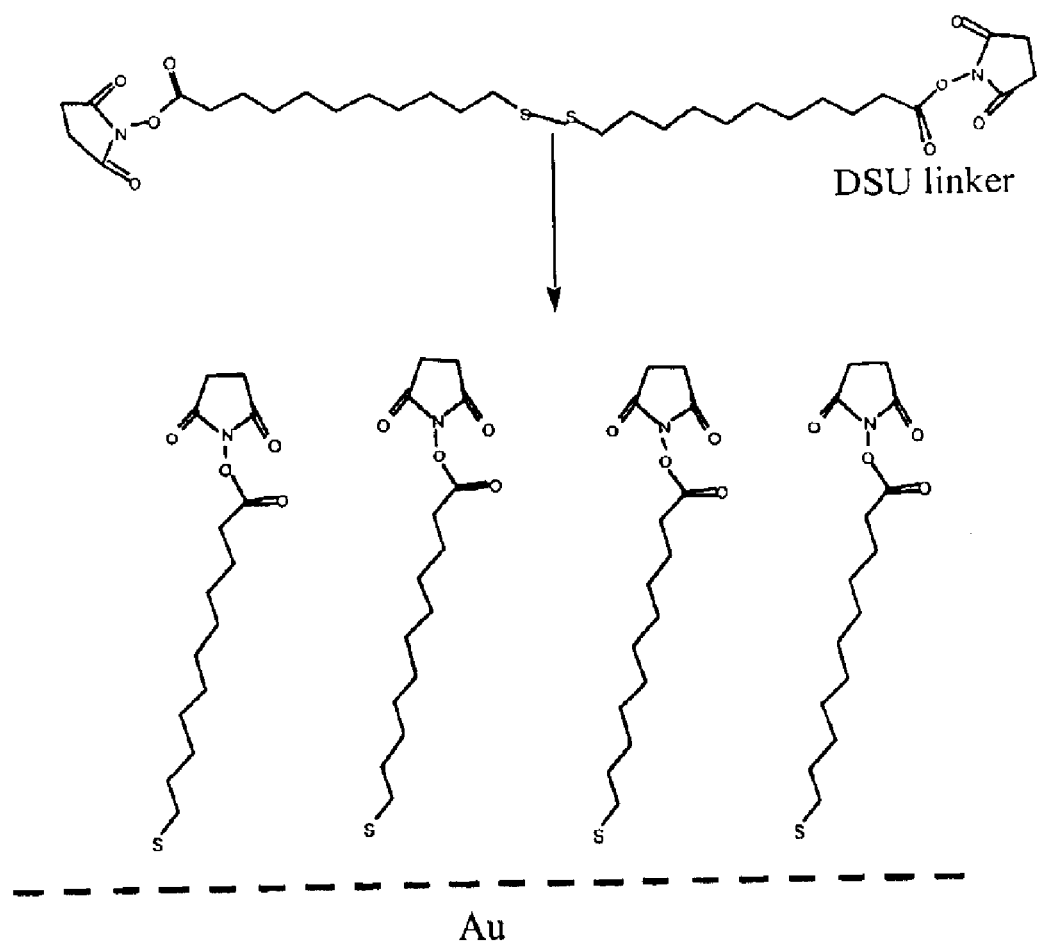
FIG. 31 shows immobilization of a DSU (dithiobissuccinirnidylundecanioate) linker on a gold surface, in which the sulfur—sulfur bond breaks and an Au—S bond forms.
Figure 32:
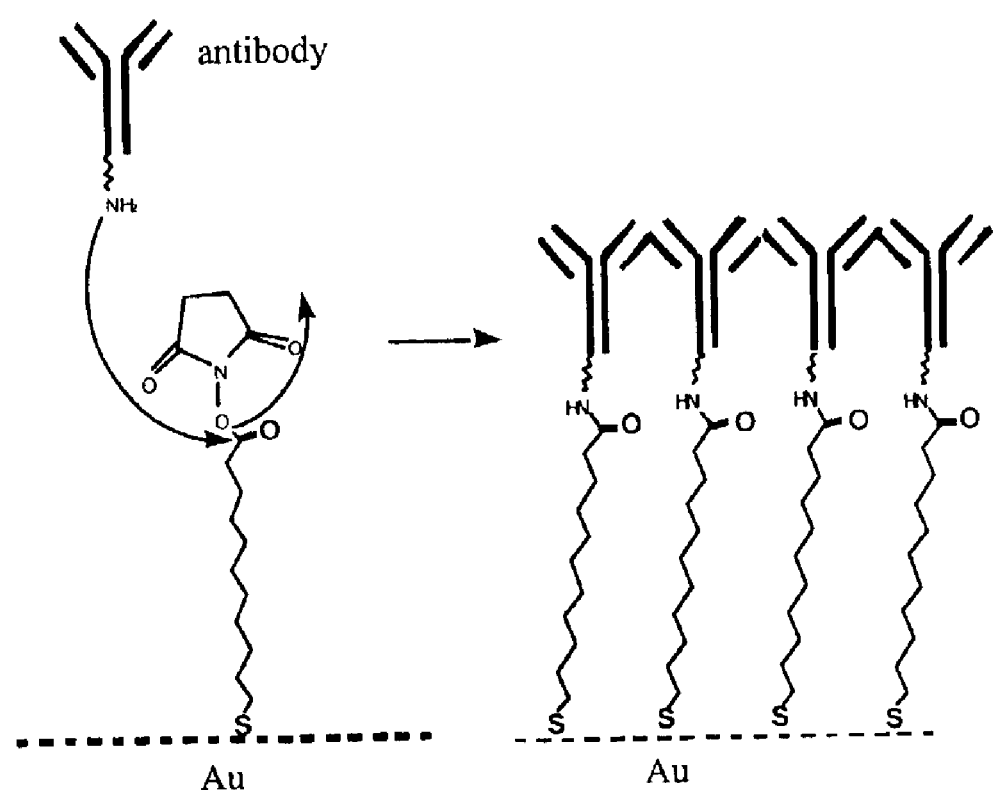
FIG. 32 shows covalent binding of antibodies with a DSU linker.

Biomolecues, such as thiols (RSH) or amines ($RNH_2$) and their derivatives, have good affinity to noble metals, particularly a gold surface, see R. G. Muzzo, D. L. Allara, Adsorption of bifunctional organic disulfides on gold surfaces, *J. Am. Chem. Soc.* 1983, 105, pp. 4481–4483; H. O. Finklea, Electrochemistry of organized monolayers of thiols and related molecules on electrodes, *Electroanal. Chem.* 1996, 19, pp. 109–335; A. Ulman, Formation and Structure of Self-Assembled Monolayers, *Chem. Rev.* 1996, 96, pp. 1553–1554, the entire contents and disclosures of which are hereby incorporated by reference. In the present invention, the gold nano posts inside the porous oxide or freely standing on a conductive surface guide the binding of these molecules and form a closely packed biorecognition layer. Besides the direct binding of antibody, a DSU (dithiobissuccinimidylundecanoate) linker has been synthesized, which will form a covalent bond with the antibody. FIG. 31 shows that a sulfur—sulfur-bond in a DSU linker molecule will break to form Au—S bond when it is close to the gold surface. The covalent immobilization of antibodies takes place when a Lysine residue of the antibody comes into contact with the DSU linker to nucleophilically attack the carbonyl carbon, thereby displacing the N-hydroxysuccinimide to form an amide linkage, as shown by FIG. 32. The application of linkers further improves the packing density of antibodies as well as the activity of the immobilized antibody and in-turn enhances the detection sensitivity. This improvement has been confirmed by optical density measurements by Enzyme Linked Immuno Sorbent Assay (ELISA). Metal nanowires, such as gold nanowire arrays etc., provide a greater density of active binding sites than a typical flat metal surface.

Electrochemical impedance spectroscopy (EIS) may be used for the analysis. The basic idea is that the nanostructured metal surface strongly secures a layer of sensing elements, such as antibodies, and those sensing elements sense the presence of the target molecules specifically. The local change of the composition or the structure of the interfacial layer changes the AC capacitance of the system, which may be quickly detected by an impedimetric sensor. The AC current flow in the cell crosses the interface by either a faradaic or nonfaradaic path. In the nonfaradaic path, interfaces are subjected to repetitive charging and discharging by dipole rotation, dipole induction, double-layer effects, etc., all of which do not produce chemical alternation of the interfaces, only varying amounts of interfacial charging. This interfacial charging is governed by the interfacial capacitance, which is the intrinsic property of the interfacial layer. Electrochemical Impedance Spectroscopy (EIS) is an electrochemical method wherein the electrode voltage is perturbed with an alternating signal of small amplitude (<10 mV) to observe the way in which the system follows the perturbation when the system is at a steady state or at equilibrium. The frequency of the applied voltage is varied over a large range (a few mili-Hz to 100,000 Hz). Impedance is a more general concept than resistance because it lakes the phase difference into account, and is furthermore a very sensitive and reproducible method. Because of the small amplitude of AC voltage applied, it is a nondestructive detection method for biosystems, avoiding the faradaic processes and many error-causing problems. The substrate with gold nano-posts sealed in the dielectric oxide layer is very suitable for the EIS measurement.

Figure 28:
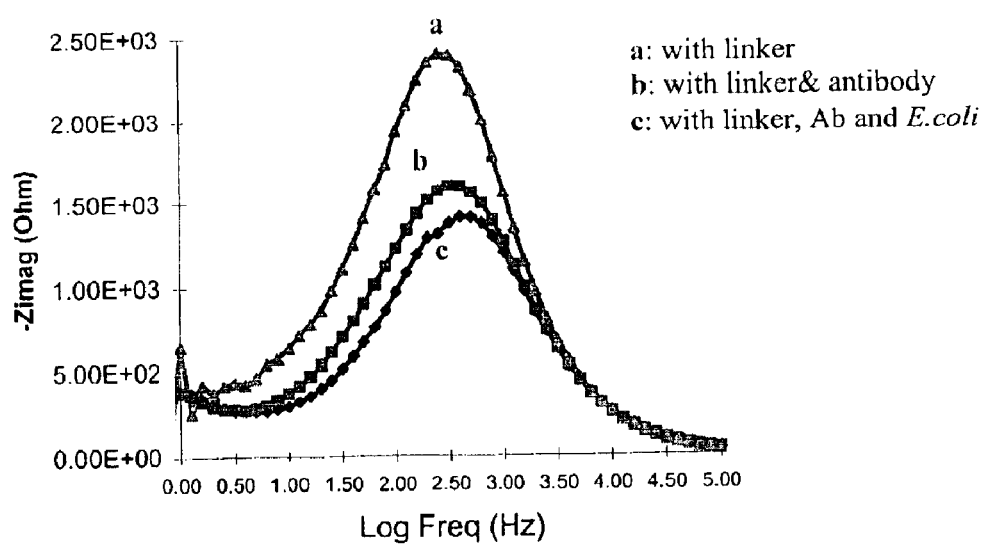
FIG. 28 shows EIS measurements of a nanogold (GNW $Al_2O_3$) sensor after different biomolecules are bound, with curve (c) illustrating the addition of $1.2 \times 10^7$ cells added to the surface.

FIG. 28 is a typical plot of EIS data collected from a nano gold posts array in alumina. A 0.178 cm² immunosensor consisting of nano gold posts in an inert matrix of Al$_2$O$_3$ was tested to be able to detect the binding of 50 E. coli cells on the nanopatterned gold surface.

Figure 29:
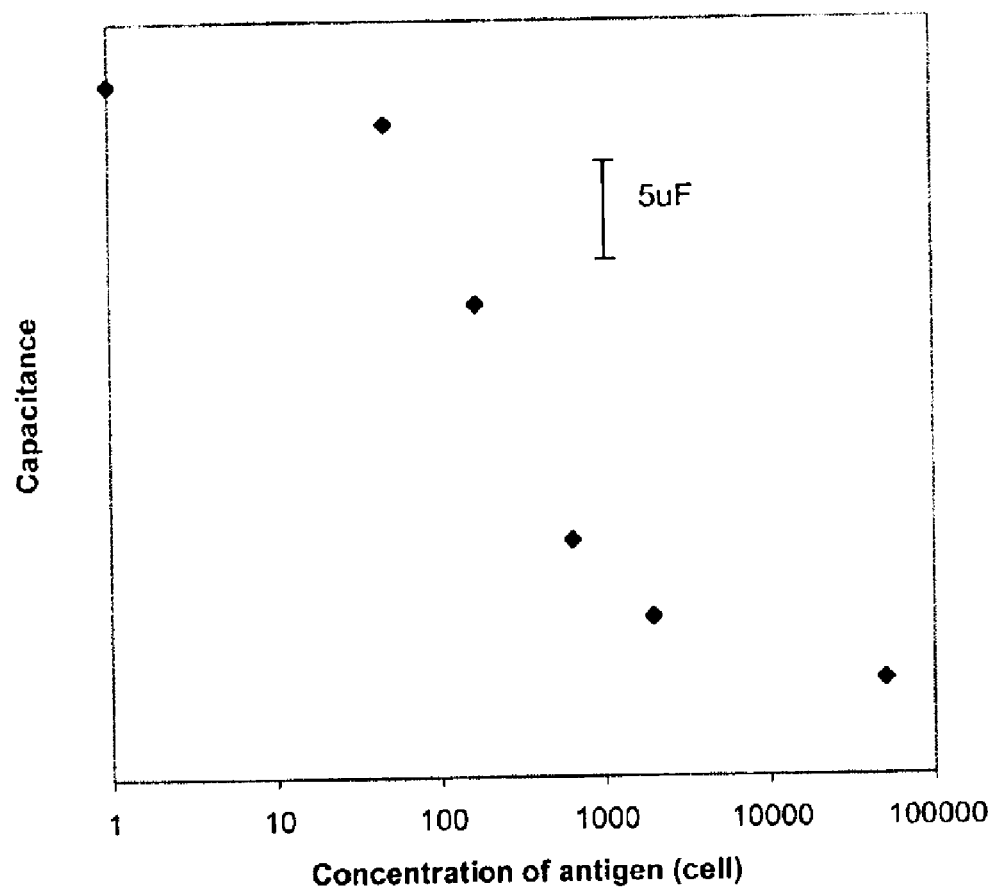
FIG. 29 shows a calibration curve illustrating capacitance v. the logarithm of E. coli concentration.

FIG. 29 shows a calibration curve relating the capacitance to the number of E. coli cells for the nano gold sensor device.

Figure 27:
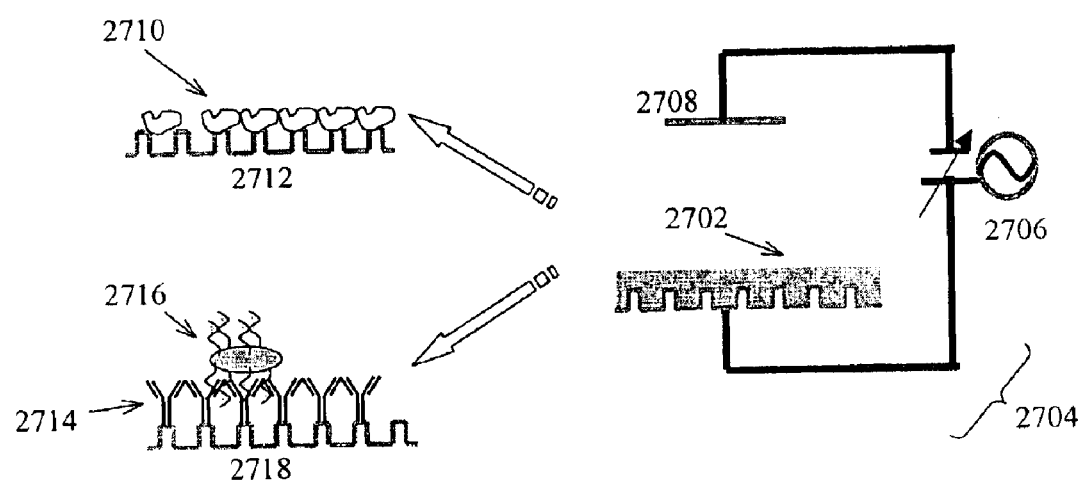
FIG. 27 shows an biosensor according to an embodiment of the present invention.

In addition to the E. coli bacteria immunosensor, the biosensing methods and apparatus of the present invention may be applied to the detection of other biomolecules, such as penicillin or other antigens or antibodies. The biorecognition elements may be the corresponding specific enzyme or antibody or antigen. FIG. 27 shows schematically a biosensor device and detection system according to the present invention. Biomembrane 2702 serves as a working electrode or nonpatterned film and is connected to circuit 2704 providing a DC or AC voltage 2706 and a counter electrode 2708. Biomembrane 2702 may be used to attach a biomolecule 2710 such as proteins, enzymes etc. such as shown in 2712, or may have integrated antibodies 2714 to bind antigen 2716, such as shown in 2718.

This nanobiosensor, such as the free-standing gold nanopost array may also be used as an amperometric sensor with extraordinarily high sensitivity and specificity due to the highly increased surface area and activity.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A multilayer thin-film based nanoporous alumina template system, comprising:
   a substrate;
   an electrode layer disposed above said substrate;
   a diffusion barrier disposed above said electrode layer, wherein said diffusion barrier comprises a member selected from the group consisting of titanium or its oxide, tantalum or its oxide, niobium or its oxide, zirconium or its oxide, and chromium or its oxide; and
   an aluminum anodization layer disposed above said diffusion barrier.

2. The multilayer thin film system of claim 1, further comprising an aluminum contact layer disposed below said substrate, wherein said substrate is below said electrode layer, said electrode layer is below said diffusion barrier and said diffusion barrier is below said aluminum anodization layer.

3. The multilayer thin film system of claim 1, further comprising an adhesion layer disposed between said electrode layer and said substrate.

4. The multilayer thin film system of claim 3, wherein said adhesion layer comprises titanium.

5. The multilayer thin film system of claim 3, wherein said adhesion layer comprises tantalum.

6. The multilayer thin film system of claim 3, wherein said adhesion layer comprises niobium.

7. The multilayer thin film system of claim 3, wherein said adhesion layer comprises zirconium.

8. The multilayer thin film system of claim 3, wherein said adhesion layer comprises chromium.

9. The multilayer thin film system of claim 1, wherein said diffusion barrier comprises titanium or its oxide.

10. The multilayer thin film system of claim 1, wherein said diffusion barrier comprises tantalum or its oxide.

11. The multilayer thin film system of claim 1, wherein said diffusion barrier comprises niobium or its oxide.

12. The multilayer thin film system of claim 1, wherein said diffusion barrier comprises zirconium or its oxide.

13. The multilayer thin film system of claim 1, wherein said diffusion barrier comprises chromium or its oxide.

14. The multilayer thin film system of claim 1, wherein said substrate comprises silicon.

15. The multilayer thin film system of claim 1, wherein said substrate comprises glass.

16. The multilayer thin film system of claim 1, wherein said substrate comprises mica.

17. The multilayer thin film system of claim 1, wherein said substrate comprises quartz.

18. The multilayer thin film system of claim 1, wherein said substrate comprises sapphire.

19. The multilayer thin film system of claim 1, wherein said electrode layer comprises platinum.

20. The multilayer thin film system of claim 1, wherein said electrode layer comprises gold.

21. The multilayer thin film system of claim 1, wherein said electrode layer comprises palladium.

22. The multilayer thin film system of claim 1, wherein said electrode layer comprises osmium.

23. The multilayer thin film system of claim 1, wherein said electrode layer comprises rhodium.

24. The multilayer thin film system of claim 1, wherein said electrode layer comprises a transparent conducting oxide.

25. The multilayer thin film system of claim 1, wherein said electrode layer comprises in-doped tin oxide.

26. An anodized multilayer thin film based nanoporous alumina system, comprising:
   a substrate;
   an electrode layer disposed above said substrate;
   a diffusion barrier disposed above said electrode layer, wherein said diffusion barrier comprises a member selected from the group consisting of titanium or its oxide, tantalum or its oxide, niobium or its oxide, zirconium or its oxide, and chromium or its oxide; and
   an aluminum anodization layer disposed above said diffusion barrier; and at least one pore extending from an upper surface of said aluminum anodization layer through at least a portion of said aluminum anodization layer.

27. The anodized multilayer thin film system of claim 26, further comprising an aluminum contact layer disposed below said substrate, wherein said substrate is below said electrode layer, said electrode layer is below said diffusion barrier and said diffusion barrier is below said aluminum anodization layer.

28. The anodized multilayer thin film system of claim 26, further comprising an adhesion layer disposed between said electrode layer and said substrate.

29. The anodized multilayer thin film system of claim 28, wherein said adhesion layer comprises titanium.

30. The anodized multilayer thin film system of claim 28, wherein said adhesion layer comprises tantalum.

31. The anodized multilayer thin film system of claim 28, wherein said adhesion layer comprises niobium.

32. The anodized multilayer thin film system of claim 28, wherein said adhesion layer comprises zirconium.

33. The anodized multilayer thin film system of claim 28, wherein said adhesion layer comprises chromium.

34. The anodized multilayer thin film system of claim 26, wherein said diffusion barrier comprises titanium oxide.

35. The anodized multilayer thin film system of claim 26, wherein said diffusion barrier comprises tantalum oxide.

36. The anodized multilayer thin film system of claim 26, wherein said diffusion barrier comprises niobium oxide.

37. The anodized multilayer thin film system of claim 26, wherein said diffusion barrier comprises zirconium oxide.

38. The anodized multilayer thin film system of claim 26, wherein said diffusion barrier comprises chromium oxide.

39. The anodized multilayer thin film system of claim 26, wherein said substrate comprises silicon.

40. The anodized multilayer thin film system of claim 26, wherein said substrate comprises glass.

41. The anodized multilayer thin film system of claim 26, wherein said substrate comprises mica.

42. The anodized multilayer thin film system of claim 26, wherein said substrate comprises quartz.

43. The anodized multilayer thin film system of claim 26, wherein said substrate comprises sapphire.

44. The anodized multilayer thin film system of claim 26, wherein said electrode layer comprises platinum.

45. The anodized multilayer thin film system of claim 26, wherein said electrode layer comprises gold.

46. The anodized multilayer thin film system of claim 26, wherein said electrode layer comprises palladium.

47. The anodized multilayer thin film system of claim 26, wherein said electrode layer comprises osmium.

48. The anodized multilayer thin film system of claim 26, wherein said electrode layer comprises rhodium.

49. The anodized multilayer thin film system of claim 26, wherein said electrode layer comprises a transparent conducting oxide.

50. The anodized multilayer thin film system of claim 26, wherein said electrode layer comprises in-doped tin oxide.

51. The multilayer thin film system of claim 26, wherein said at least one pore extends through said aluminum anodization layer and said diffusion barrier.

52. The multilayer thin film system of claim 26, wherein said at least one pore has a diameter of approximately 5 to approximately 200 nm.

53. The multilayer thin film system of claim 26, wherein said at least one pore has a depth of approximately 100 $\mu$m or less.

* * * * *